US007435747B2

(12) United States Patent
Peyman et al.

(10) Patent No.: US 7,435,747 B2
(45) Date of Patent: Oct. 14, 2008

(54) GUANIDINE AND AMIDINE DERIVATIVES AS FACTOR XA INHIBITORS

(75) Inventors: Anuschirwan Peyman, Kelkheim (DE); David William Will, Kriftel (DE); Uwe Gerlach, Hattersheim (DE); Marc Nazaré, Eppstein (DE); Gerhard Zoller, Schöneck (DE); Hans-Peter Nestler, Kelkheim (DE); Hans Matter, Langenselbold (DE); Fahad Al-Obeidi, Tucson, AZ (US)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 552 days.

(21) Appl. No.: 10/886,312

(22) Filed: Jul. 7, 2004

(65) Prior Publication Data
US 2005/0143419 A1 Jun. 30, 2005

Related U.S. Application Data

(63) Continuation of application No. 10/004,422, filed on Dec. 6, 2001, now abandoned.

(30) Foreign Application Priority Data

Dec. 6, 2000 (EP) .................................. 00126750

(51) Int. Cl.
*A61K 31/445* (2006.01)
*C07D 211/26* (2006.01)
(52) U.S. Cl. ........................ 514/331; 514/326; 514/364; 546/209; 546/229; 548/131; 564/225
(58) Field of Classification Search ................. 514/326, 514/331, 364; 546/209, 229; 548/131; 564/225
See application file for complete search history.

(56) References Cited

U.S. PATENT DOCUMENTS

| 5,260,307 | A | * | 11/1993 | Ackermann et al. | ......... 514/323 |
| 5,792,769 | A | | 8/1998 | Lu et al. | |
| 6,277,865 | B1 | | 8/2001 | Klein | |
| 6,417,200 | B1 | * | 7/2002 | Beight et al. | ................ 514/330 |
| 2002/0016339 | A1 | * | 2/2002 | Klein et al. | .................. 514/318 |

FOREIGN PATENT DOCUMENTS

| EP | 976722 | * | 2/2000 |
| EP | 0987274 | | 3/2000 |
| WO | WO 92/06711 | | 4/1992 |
| WO | WO 95/29189 | | 11/1995 |
| WO | WO 96/04267 | | 2/1996 |
| WO | WO 96/12800 | | 5/1996 |
| WO | WO 97/28129 | | 8/1997 |
| WO | WO 97/47651 | | 12/1997 |
| WO | WO 99/48870 | | 9/1999 |
| WO | WO 01/19788 | | 3/2001 |

OTHER PUBLICATIONS

Honna et al. "1-N-amidino . . . " CA 91:193292 (1979).*
Kawamoto et al. "Preparation of 2-(2-carbamoyl-4-pyrrolidinylthiocarbapenems as antibiotics" CA 120:269926 (1994).*
Andereson et al. "Nonpeptide GnRH agents . . . " CA 132:279106 (2000).*
Levesque et al. "Novel bicyclic lactam inhibitors of thrombin . . . " CA 136:210039 (2001).*
Ackerman et al. "Preparation of amidino . . . " CA 116:214908 (1992).*
Hendrix et al. "Preparation of heterocyclic . . . " CA 137:201331 (2002).*
Rubini et al. "Synthesis of isosteric . . . " Tetrahedron v.42 p. 6039-45 (1986).*
King "Bioisosteres, conformational . . . " Med. Che. Principle and Practice (1994) p. 206-208.*
Adang Anton E P et al., A New Generation of Orally Active Antithrombotics: Comparing Strategies in the GBIIb/IIIa, Thrombin and Factor Xa Areas, Drugs of the Future 2000; vol. 25(4); pp. 369-383.
Bundgaard, Hans, Novel Chemical Approaches in Prodrug Design, Drugs of the Future, (1991), vol. 16, No. 5, pp. 443-458.

(Continued)

Primary Examiner—Celia Chang
(74) Attorney, Agent, or Firm—Jiang Lin

(57) ABSTRACT

The present invention relates to compounds of the formula I,

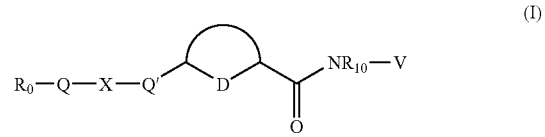

in which $R_0$; Q; X; Q', D, $R_{10}$ and V have the meanings indicated in the claims. The compounds of the formula I are valuable pharmacologically active compounds. They exhibit a strong antithrombotic effect and are suitable, for example, for the therapy and prophylaxis of cardiovascular disorders like thromboembolic diseases or restenoses. They are reversible inhibitors of the blood clotting enzymes factor Xa (FXa) and/or factor VIIa (FVIIa), and can in general be applied in conditions in which an undesired activity of factor Xa and/or factor VIIa is present or for the cure or prevention of which an inhibition of factor Xa and/or factor VIIa is intended. The invention furthermore relates to processes for the preparation of compounds of the formula I, their use, in particular as active ingredients in pharmaceuticals, and pharmaceutical preparations comprising them.

5 Claims, No Drawings

OTHER PUBLICATIONS

Carpino, L., 1-Hydroxy-7-Azabenzotriazole. An Efficient Peptide Coupling Additive, J. Am. Chem. Soc. 1993, vol. 115, pp. 4397-4398.

Cheng Yung-Chi et al., Relationship Between the Inhibition Constant (K1) and the Concentration of Inhibitor which causes 50 per cent Inhibition (I 50) of an Enzymatic Reaction, Biochem. Pharmacol., 1973, vol. 22, pp. 3099-3108.

Fleisher David et al., Improved Oral Drug Delivery: Solubility Limitations Overcome by the Use of Prodrugs, Advanced Drug Delivery Reviews; 1996; vol. 19; pp. 115-130.

Giralt, E., Peptides 1990, Proceedings of the Twenty-First European Peptide Symposium Sep. 2-8, 1990, Platja d'Aro, Spain pp. 143-145, 1991.

Ostrem James A et al., Discovery of a Novel, Potent, and Specific Family of Factor Xa Inhibitors via Combinatorial Chemistry, Biochemistry, 1998, vol. 37, pp. 1053-1059.

Segel Irwin H, Behavior and Analysis of Rapid Equilibrium and Steady-State Enzyme Systems, Enzyme Kinetics, 1975, John Wiley & Sons, New York, pp. 100-125.

* cited by examiner

GUANIDINE AND AMIDINE DERIVATIVES AS FACTOR XA INHIBITORS

This application is a Continuation of application Ser. No. 10/004,422, filed Dec. 6, 2001.

FIELD OF THE INVENTION

The present invention relates to compounds of the formula I,

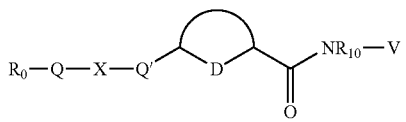

in which $R_0$; Q; X; Q', D, $R_{10}$ and V have the meanings indicated below. The compounds of the formula I are valuable pharmacologically active compounds. They exhibit a strong antithrombotic effect and are suitable, for example, for the therapy and prophylaxis of cardiovascular disorders like thromboembolic diseases or restenoses. They are reversible inhibitors of the blood clotting enzymes factor Xa (FXa) and/or factor VIIa (FVIIa), and can in general be applied in conditions in which an undesired activity of factor Xa and/or factor VIIa is present or for the cure or prevention of which an inhibition of factor Xa and/or factor VIIa is intended. The invention furthermore relates to processes for the preparation of compounds of the formula I, their use, in particular as active ingredients in pharmaceuticals, and pharmaceutical preparations comprising them.

BACKGROUND OF THE INVENTION

Normal haemeostasis is the result of a complex balance between the process of clot initiation, formation and clot dissolution. The complex interactions between blood cells, specific plasma proteins and the vascular surface, maintain the fluidity of blood unless injury and blood loss occurs (EP-A-987274). Many significant disease states are related to abnormal haemostasis. For example, local thrombus formation due to rupture of atheroslerotic plaque is a major cause of acute myocardial infarction and unstable agina. Treatment of an occlusive coronary thrombus by either thrombolytic therapy or percutaneous angioplasty may be accompanied by acute thrombolytic reclosure of the affected vessel.

There continues to be a need for safe and effective therapeutic anticoagulants to limit or prevent thrombus formation. It is most desirable to develop agents that inhibit coagulation without directly inhibiting thrombin but by inhibiting other steps in the coagulation cascade like factor Xa and/or factor VIIa activity. It is now believed that inhibitors of factor Xa carry a lower bleeding risk than thrombin inhibitors (A. E. P. Adang & J. B. M. Rewinkel, Drugs of the Future 2000, 25, 369-383).

Low molecular weight, factor Xa-specific blood clotting inhibitors that are effective but do not cause unwanted side effects have been described, for example, in WO-A-95/29189. However, besides being an effective factor Xa-specific blood clotting inhibitor, it is desirable that such inhibitors also have further advantageous properties, for instance stability in plasma and liver and selectivity versus other serine proteases whose inhibition is not intended, such as thrombin.

There is an ongoing need for further low molecular weight factor Xa specific blood clotting inhibitors which are effective and have the above advantages as well.

Specific inhibition of the factor VIIa/tissue factor catalytic complex using monoclonal antibodies (WO-A-92/06711) or a protein such as chloromethyl ketone inactivated factor VIIa (WO-A-96/12800, WO-A-97/47651) is an extremely effective means of controlling thrombus formation caused by acute arterial injury or the thrombotic complications related to bacterial septicemia. There is also experimental evidence suggesting that inhibition of factor VIIa/tissue factor activity inhibits restenosis following balloon angioplasty. Bleeding studies have been conducted in baboons and indicate that inhibition of the factor VIIa/tissue factor complex has the widest safety window with respect to therapeutic effectiveness and bleeding risk of any anticoagulant approach tested including thrombin, platelet and factor Xa inhibition. Certain inhibitors of factor VIIa have already been described. EP-A-987274, for example discloses compounds containing a tripeptide unit which inhibit factor VIIa. However, the property profile of these compounds is still not ideal, and there is an ongoing need for further low molecular weight factor VIIa inhibitory blood clotting inhibitors.

The present invention satisfies the above needs by providing novel compounds of the formula I which exhibit factor Xa and/or factor VIIa inhibitory activity and are favorable agents for inhibiting unwanted blood clotting and thrombus formation.

SUMMARY OF THE INVENTION

The present invention relates to compounds of the formula I,

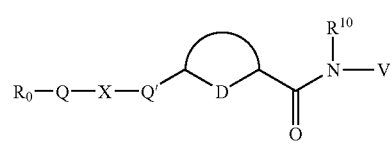

wherein
$R_0$ is 1. phenyl, wherein phenyl is unsubstituted or mono-, di- or trisubstituted independently of one another by $R^2$ or
  2. a mono- or bicyclic 5- to 10-membered heteroaryl containing one or two nitrogen atoms as ring heteroatoms, wherein heteroaryl is unsubstituted or mono-, di- or trisubstituted independently of one another by $R^2$,
$R^2$ is 1. —$NO_2$,
  2. halogen,
  3. —CN,
  4. —OH,
  5. —$NH_2$,
  6. ($C_1$-$C_8$)-alkyloxy-, wherein alkyloxy is unsubstituted or mono-, di- or trisubstituted independently of one another by halogen, amino group, hydroxy group or methoxy group, or
  7. —($C_1$-$C_8$)-alkyl, wherein alkyl is unsubstituted or mono-, di- or trisubstituted independently of one another by halogen, amino group, hydroxy group or methoxy group,
Q and Q' are independently of one another identical or different and are a direct bond, —O—, —S—, —$NR^{10}$—, —C(O)$NR^{10}$—, —$NR^{10}$C(O)—, —S(O)—, —$SO_2$—, —$NR^{10}$—$SO_2$—, —$SO_2$—$NR^{10}$— oder —C(O)—;

$R^{10}$ is hydrogen atom or $(C_1-C_4)$-alkyl-,

X is 1. a direct bond,
  2. $(C_1-C_6)$-alkylene, wherein alkylene is unsubstituted or mono-, di- or trisubstituted independently of one another by halogen, amino group or hydroxy group,
  3. $(C_3-C_6)$-cycloalkylene, wherein cycloalkylene is unsubstituted or mono-, di- or trisubstituted independently of one another by halogen, amino group or hydroxy group, provided that at least one of Q, X and Q' is not a direct bond,
D is an atom out of the group carbon, oxygen, sulfur and nitrogen, the substructure of formula III

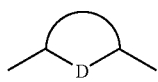
(III)

is 1. a mono- or bicyclic 5- to 10-membered carbocyclic aryl group, wherein said 5- to 10-membered carbocyclic aryl group is unsubstituted or mono-, di- or trisubstituted independently of one another by $R^1$,
  2. phenyl, wherein phenyl is unsubstituted or mono-, di- or trisubstituted independently of one another by $R^1$,
  3. a mono- or bicyclic 5- to 10-membered heterocyclic group (Het), containing one or more heteroatoms as ring heteroatoms, such as nitrogen, sulfur or oxygen, wherein said Het group is unsubstituted or mono-, di- or trisubstituted independently of one another by $R^1$, or
  4. pyridyl, wherein pyridyl is unsubstituted or mono-, di- or trisubstituted independently of one another by $R^1$, $R^1$ is 1. halogen,
  2. $-NO_2$,
  3. $-CN$,
  4. $R^{11}R^{12}N-$, wherein $R^{11}R^{12}$ independently of one another are hydrogen atom, $(C_1-C_4)$-alkyl- or $(C_1-C_6)$-acyl-,
  5. $(C_1-C_8)$-alkylamino-, wherein alkyl is unsubstituted or mono-, di- or trisubstituted independently of one another by $R^{13}$,
  6. $-OH$,
  7. $-SO_2-NH_2$,
  8. $(C_1-C_8)$-alkyloxy-, wherein alkyl is unsubstituted or mono-, di- or trisubstituted independently of one another by $R^{13}$,
  9. $(C_6-C_{14})$-aryl, wherein aryl is unsubstituted or mono-, di- or trisubstituted independently of one another by $R^{13}$,
  10. $(C_1-C_8)$-alkyl-, wherein alkyl is unsubstituted or mono-, di- or trisubstituted independently of one another by $R^{13}$,
  11. hydroxycarbonyl-$(C_1-C_8)$-alkylureido-, wherein alkyl is unsubstituted or mono-, di- or trisubstituted independently of one another by $R^{13}$,
  12. $(C_1-C_8)$-alkyloxycarbonyl-$(C_1-C_8)$-alkylureido-, wherein alkyl is unsubstituted or mono-, di- or trisubstituted independently of one another by $R^{13}$,
  13. $(C_1-C_8)$-alkylsulfonyl-, wherein alkyl is unsubstituted or mono-, di- or trisubstituted independently of one another by $R^{13}$, or
  14. $-C(O)-NR^{14}R^{15}$, wherein $R^{14}R^{15}$ independently of one another are hydrogen atom or $(C_1-C_4)$-alkyl-, or two $R^1$ residues bonded to adjacent ring carbon atoms together with the carbon atoms to which they are bonded form an aromatic ring condensed to the ring depicted in formula I, where the ring formed by the two $R^1$ residues is unsubstituted or mono-, di- or trisubstituted independently of one another by $R^{13}$, or $R^{11}$ and $R^{12}$ together with the nitrogen atom to which they are bonded form a saturated or unsaturated 5- to 6-membered monocyclic heterocyclic ring which in addition to the nitrogen atom carrying $R^{11}$ and $R^{12}$ can contain one or two identical or different ring heteroatoms chosen from oxygen, sulfur and nitrogen, and in which one or two of the ring carbon atoms can be substituted by oxo to form $-C(O)-$ residue(s), $R^{13}$ is 1. halogen,
  2. $-NO_2$,
  3. $-CN$,
  4. $-OH$,
  5. $(C_1-C_8)$-alkyl-,
  6. $(C_1-C_8)$-alkyloxy-,
  7. $-CF_3$ or
  8. $-NH_2$, V is a residue of the formulae IIa, IIb, IIc, IId, IIe or IIf,

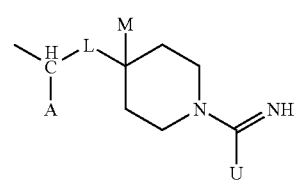
IIa

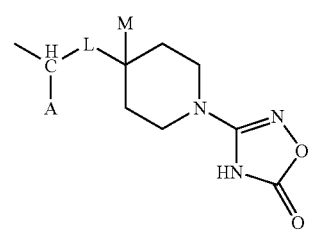
IIb

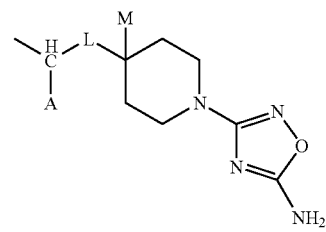
IIe

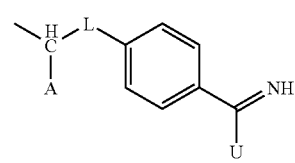
IIc

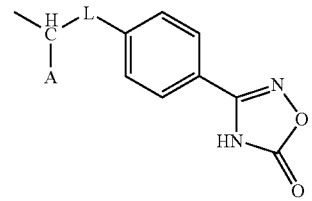
IId

-continued

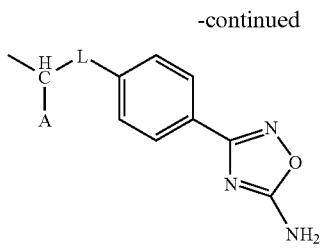

IIf wherein

L is is a direct bond or ($C_1$-$C_3$)-alkylene, wherein alkylene is unsubstituted or mono-, di- or trisubstituted independently of one another by A, A is 1. hydrogen atom,
2. —C(O)—OH,
3. —C(O)—O—($C_1$-$C_4$)-alkyl, wherein alkyl is unsubstituted or mono-, di- or trisubstituted independently of one another by —OH, —$NH_2$ or —($C_1$-$C_4$)-alkoxy,
4. —C(O)—$NR^4R^5$,
5. ($C_1$-$C_4$)-alkyl-, wherein alkyl is unsubstituted or mono-, di- or trisubstituted independently of one another by —OH, —$NH_2$ or —($C_1$-$C_4$)-alkoxy,
6. —$SO_2$—$NH_2$ or
7. —$SO_2$—$CH_3$, U is —$NH_2$, ($C_1$-$C_4$)-alkyl-,—NH—C(O)—O—($C_1$-$C_4$)-alkyl or —NH—C(O)—O—($C_1$-$C_4$)-alkyl-aryl, M is hydrogen atom, ($C_1$-$C_3$)-alkyl- or —OH, $R^4$ and $R^5$ are independently of one another identical or different and are
1. hydrogen atom,
2. ($C_1$-$C_{12}$)-alkyl-, wherein alkyl is unsubstituted or mono-, di- or trisubstituted independently of one another by $R^{13}$ as defined above,
3. ($C_6$-$C_{14}$)-aryl-($C_1$-$C_4$)-alkyl-, wherein alkyl and aryl are unsubstituted or mono-, di- or trisubstituted independently of one another by $R^{13}$ as defined above,
4. ($C_6$-$C_{14}$)-aryl-, wherein aryl is unsubstituted or mono-, di- or trisubstituted independently of one another by $R^{13}$ as defined above,
5. Het-, wherein Het- is unsubstituted or mono-, di- or trisubstituted independently of one another by $R^{13}$ as defined above, or
6. Het-($C_1$-$C_4$)-alkyl-, wherein alkyl and Het- are unsubstituted or mono-, di- or trisubstituted independently of one another by $R^{13}$ as defined above, or $R^4$ and $R^5$ together with the nitrogen atom to which they are bonded form a saturated 3- to 8-membered monocyclic heterocyclic ring which in addition to the nitrogen atom carrying $R^4$ and $R^5$ can contain one or two identical or different ring heteroatoms chosen from oxygen, sulfur and nitrogen;

in all its stereoisomeric forms and mixtures thereof in any ratio, and its physiologically tolerable salts.

DETAILED DESCRIPTION OF THE INVENTION

Preferred are compounds of the formula I, wherein $R_0$ is phenyl, wherein phenyl is unsubstituted or mono-, di- or trisubstituted independently of one another by $R^2$, or pyridyl, wherein pyridyl is unsubstituted or mono-, di- or trisubstituted independently of one another by $R^2$, $R^2$ is 1. —$NO_2$,
2. halogen,
3. —CN,
4. —OH,
5. —$NH_2$,
6. ($C_1$-$C_4$)-alkyloxy-, wherein alkyloxy is unsubstituted or mono-, di- or trisubstituted independently of one another by halogen, amino group, hydroxy group or methoxy group, or
7. —($C_1$-$C_4$)-alkyl, wherein alkyl is unsubstituted or mono-, di- or trisubstituted independently of one another by halogen, amino group, hydroxy group or methoxy group, Q, Q', X, $R^1$, $R^{11}$ and $R^{12}$ are as defined above, D is an atom out of the group carbon and nitrogen, the substructure of formula III is
1. phenyl, wherein phenyl is unsubstituted or mono-, di- or trisubstituted independently of one another by $R^1$, or
2. pyridyl, wherein pyridyl is unsubstituted or mono-, di- or trisubstituted independently of one another by $R^1$, $R^{13}$ is 1. halogen,
2. —$NO_2$,
3. —CN,
4. —OH,
5. ($C_1$-$C_4$)-alkyl-,
6. ($C_1$-$C_4$)-alkyloxy-,
7. —$CF_3$ or
8. —$NH_2$, $R_{10}$ is hydrogen atom or methyl, V is a fragment of the formula IIa, IIb, IIc, IId, IIe or IIf as defined above, wherein L, U, M, $R^4$ and $R^5$ are as defined above, and A is 1. hydrogen atom,
2. —C(O)—OH,
3. —C(O)—O—($C_1$-$C_4$)-alkyl, wherein alkyl is unsubstituted or mono-, di- or trisubstituted independently of one another by —OH, —$NH_2$ or —($C_1$-$C_4$)-alkoxy,
4. —C(O)—$NR^4R^5$ or
5. ($C_1$-$C_4$)-alkyl-, wherein alkyl is unsubstituted or mono-, di- or trisubstituted independently of one another by —OH, —$NH_2$ or —($C_1$-$C_4$)-alkoxy.

More preferred are compounds of the formula I, wherein

R is phenyl, wherein phenyl is mono-, di- or trisubstituted independently of one another by $R^2$, or
pyridyl, wherein pyridyl is mono-, di- or trisubstituted independently of one another by $R^2$, $R^2$ is 1. —$NH_2$,
2. halogen,
3. —CN,
4. —OH,
5. ($C_1$-$C_4$)-alkyloxy-, wherein alkyloxy is unsubstituted or substituted by an amino group, or
6. —($C_1$-$C_4$)-alkyl, wherein alkyl is unsubstituted or substituted by an amino group, Q and Q' are independently of one another identical or different and are a direct bond, —O—, —C(O)$NR^{10}$—, —$NR^{10}$C(O)—; —$NR^{10}$—$SO_2$—; or —$SO_2$—$NR^{10}$—;

X is 1. a direct bond or
2. ($C_1$-$C_4$)-alkylene, wherein alkylene is unsubstituted or mono-, di- or trisubstituted independently of one another by halogen, amino group or hydroxy group, D is an atom out of the group carbon and nitrogen, the substructure of formula III is
phenyl or pyridyl, wherein phenyl and pyridyl are unsubstituted or mono-, di- or trisubstituted independently of one another by $R^1$, $R^1$ is 1. halogen,
2. —$NO_2$, 3. —CN,
4. —NH$_2$,
5. (C$_1$-C$_4$)-alkylamino-, wherein alkyl is unsubstituted or mono-, di- or trisubstituted independently of one another by R$^{13}$,
6. —OH,
7. —SO$_2$—NH$_2$,
8. (C$_1$-C$_4$)-alkyloxy-, wherein alkyl is unsubstituted or mono-, di- or trisubstituted independently of one another by R$^{13}$,
9. (C$_6$-C$_{14}$)-aryl, wherein aryl is unsubstituted or mono-, di- or trisubstituted independently of one another by R$^{13}$,
10. (C$_1$-C$_4$)-alkyl-, wherein alkyl is unsubstituted or mono-, di- or trisubstituted independently of one another by R$^{13}$,
11. (C$_1$-C$_4$)-alkylsulfonyl-, wherein alkyl is unsubstituted or mono-, di- or trisubstituted independently of one another by R$^{13}$,
12. —C(O)—NR$^{14}$R$^{15}$, wherein R$^{14}$R$^{15}$ independently of one another are hydrogen atom or (C$_1$-C$_4$)-alkyl-,
13. R$^{11}$R$^{12}$N—, wherein R$^{11}$ and R$^{12}$ are as defined above, or
14. —NR$^4$R$^5$, R$^{13}$ is 1. halogen,
2. —NO$_2$,
3. —CN,
4. —OH,
5. (C$_1$-C$_4$)-alkyl-,
6. (C$_1$-C$_4$)-alkyloxy-,
7. —CF$_3$ or
8. —NH$_2$, R$_{10}$ is hydrogen atom or methyl, V is a fragment of the formula IIa, IIb, IIc, IId, IIe or IIf as defined above, wherein
L is a direct bond or (C$_1$-C$_3$)-alkylen-,
A is hydrogen atom, —C(O)—OH, —C(O)—O—(C$_1$-C$_4$)-alkyl, —C(O)—NR$^4$R$^5$ or (C$_1$-C$_4$)-alkyl,
U is —NH$_2$, methyl, —NH—C(O)—O—(C$_1$-C$_4$)-alkyl or —NH—C(O)—O—(CH$_2$)-phenyl,
M is hydrogen atom, (C$_1$-C$_3$)-alkyl- or —OH, and
R$^4$ and R$^5$ are independently of one another hydrogen atom or (C$_1$-C$_4$)-alkyl-.

Even more preferred are the compounds of the formula I, wherein
R$_0$ is phenyl or pyridyl, wherein phenyl and pyridyl independently from one another are mono-, di- or trisubstituted independently of one another by R$^2$,
R$^2$ is 1. halogen,
2. —CN,
3. (C$_1$-C$_4$)-alkyloxy-, wherein alkyloxy is unsubstituted or substituted by halogen or an amino group, or
4. —(C$_1$-C$_4$)-alkyl, wherein alkyl is unsubstituted or substituted by an amino group or halogen,
Q and Q' are independently of one another identical or different and are a direct bond, —O—, —C(O)NR$^{10}$—, —NR$^{10}$C(O)—; —NR$^{10}$—SO$_2$—; or —SO$_2$—NR$^{10}$—;
X is —(C$_1$-C$_3$)-alkylene, wherein alkylene is unsubstituted or mono-, di- or trisubstituted independently of one another by halogen, amino group or hydroxy group,
D is the atom carbon,
the substructure of formula III is
phenyl, wherein phenyl is unsubstituted or mono-, di- or trisubstituted independently of one another by R$^1$,
R$^1$ is 1. halogen,
2. —NO$_2$,
3. —CN,
4. —NH$_2$,
5. (C$_1$-C$_4$)-alkylamino-, wherein alkyl is unsubstituted or mono-, di- or trisubstituted independently of one another by R$^{13}$,
6. —OH,
7. —SO$_2$—NH$_2$,
8. (C$_1$-C$_4$)-alkyloxy-, wherein alkyl is unsubstituted or mono-, di- or trisubstituted independently of one another by R$^{13}$,
9. (C$_6$-C$_{14}$)-aryl, wherein aryl is unsubstituted or mono-, di- or trisubstituted independently of one another by R$^{13}$,
10. (C$_1$-C$_4$)-alkyl-, wherein alkyl is unsubstituted or mono-, di- or trisubstituted independently of one another by R$^{13}$,
11. (C$_1$-C$_4$)-alkylsulfonyl-, wherein alkyl is unsubstituted or mono-, di- or trisubstituted independently of one another by R$^{13}$,
12. —C(O)—NR$^{14}$R$^{15}$, wherein R$^{14}$R$^{15}$ independently of one another are hydrogen atom or (C$_1$-C$_4$)-alkyl-,
13. R$^{11}$R$^{12}$N—, wherein R$^{11}$ and R$^{12}$ are as defined above, or
14. —NR$^4$R$^5$, wherein R$^4$ and R$^5$ are independently of one another hydrogen atom or methyl R$^{13}$ is 1. halogen,
2. —CF$_3$,
3. —NH$_2$,
4. —OH,
5. (C$_1$-C$_4$)-alkyl- or
6. (C$_1$-C$_4$)-alkyloxy-, R$_{10}$ is hydrogen atom, and V is a fragment of the formula IIa, IIb, IIc or IId as defined above, wherein
L is a direct bond or (C$_1$-C$_2$)-alkylen-,
A is hydrogen atom, —C(O)—OH, —C(O)—O—(C$_1$-C$_4$)-alkyl, —C(O)—NR$^4$R$^5$ or (C$_1$-C$_4$)-alkyl,
U is —NH$_2$, methyl, —NH—C(O)—O—(C$_1$-C$_4$)-alkyl or —NH—C(O)—O—(CH$_2$)-phenyl,
M is hydrogen atom or (C$_1$-C$_3$)-alkyl-.

Further preferred are compounds of the formula I, wherein
R$_0$ is phenyl, wherein phenyl is mono-, di- or trisubstituted independently of one another by R$^2$,
R$^2$ is 1. halogen,
2. (C$_1$-C$_4$)-alkyloxy-, wherein alkyloxy is unsubstituted or substituted by halogen or an amino group, or
3. —(C$_1$-C$_4$)-alkyl, wherein alkyl is unsubstituted or substituted by an amino group or halogen,
Q and Q' are independently of one another identical or different and are a direct bond, —O—, —C(O)NR$^{10}$—, —NR$^{10}$C(O)—; —NR$^{10}$—SO$_2$—; or —SO$_2$—NR$^{10}$—;
X is —(C$_1$-C$_3$)-alkylene,
D is the atom carbon, the substructure of formula III is
phenyl, wherein phenyl is unsubstituted or mono-, di- or trisubstituted independently of one another by R$^1$,
R$^1$ is 1. halogen,
2. —NO$_2$,
3. —CN,
4. —NH$_2$,
5. (C$_1$-C$_4$)-alkylamino-, wherein alkyl is unsubstituted or mono-, di- or trisubstituted independently of one another by R$^{13}$,
6. —OH,
7. —SO$_2$—NH$_2$,
8. (C$_1$-C$_4$)-alkyloxy-, wherein alkyl is unsubstituted or mono-, di- or trisubstituted independently of one another by R$^{13}$, 9. $(C_1-C_4)$-alkyl-, wherein alkyl is unsubstituted or mono-, di- or trisubstituted independently of one another by $R^{13}$,
10. $(C_1-C_4)$-alkylsulfonyl-, wherein alkyl is unsubstituted or mono-, di- or trisubstituted independently of one another by $R^{13}$,
11. —C(O)—NR$^{14}$R$^{15}$, wherein R$^{14}$R$^{15}$ independently of one another are hydrogen atom or $(C_1-C_2)$-alkyl-,
12. R$^{11}$R$^{12}$N—, wherein R$^{11}$ and R$^{12}$ are as defined above, or
13. —NR$^4$R$^5$, R$^{13}$ is 1. halogen,
  2. —CF$_3$,
  3. —NH$_2$,
  4. —OH,
  5. $(C_1-C_4)$-alkyl- or
  6. $(C_1-C_4)$-alkyloxy-, R$_{10}$ is hydrogen atom, and V is a fragment of the formula IIa, IIb, IIc or IId as defined above, wherein L is a direct bond or $(C_1-C_2)$-alkylen-, A is hydrogen atom, —C(O)—OH, —C(O)—O—$(C_1-C_4)$-alkyl, —C(O)—NR$^4$R$^5$ or —$(C_1-C_4)$-alkyl, U is —NH$_2$, methyl, —NH—C(O)—O—$(C_1-C_4)$-alkyl or —NH—C(O)—O—(CH$_2$)-phenyl, M is hydrogen atom or methyl, and R$^4$ and R$^5$ are independently of one another hydrogen atom or methyl.

Particularly preferred are compounds of the formula I, wherein

R$_0$ is phenyl, wherein phenyl is disubstituted independently of one another by R$^2$, R$^2$ is 1. halogen,
  2. $(C_1-C_2)$-alkyloxy-, wherein alkyloxy is unsubstituted or substituted by an amino group, or
  3. —$(C_1-C_4)$-alkyl, wherein alkyl is unsubstituted or substituted by an amino group, Q and Q' are independently of one another identical or different and are
  a direct bond or —O—, X is —CH$_2$—CH$_2$—, D is the atom carbon, the substructure of formula III is
  phenyl, wherein phenyl is unsubstituted or mono-, di- or trisubstituted independently of one another by R$^1$, R$^1$ is 1. halogen,
  2. —OH,
  3. —NH$_2$,
  4. —C(O)—NR$^{14}$R$^{15}$, wherein R$^{14}$R$^{15}$ independently of one another are hydrogen atom or $(C_1-C_2)$-alkyl-,
  5. $(C_1-C_3)$-alkyloxy-, wherein alkyl is unsubstituted or mono-, di- or trisubstituted independently of one another by R$^{13}$, or
  6. $(C_1-C_3)$-alkyl-, wherein alkyl is unsubstituted or mono-, di- or trisubstituted independently of one another by R$^{13}$, R$^{13}$ is fluorine or chlorine, R$_{10}$ is hydrogen atom, and V is a fragment of the formula IIa, IIb, IIc or IId as defined above, wherein L is a direct bond or $(C_1-C_2)$-alkylen-, A is hydrogen atom, —C(O)—OH, —C(O)—O—$(C_1-C_4)$-alkyl, —C(O)—NR$^4$R$^5$ or —$(C_1-C_4)$-alkyl, U is —NH$_2$, methyl, —NH—C(O)—O—$(C_1-C_4)$-alkyl or —NH—C(O)—O—(CH$_2$)-phenyl, M is hydrogen atom, and R$^4$ and R$^5$ are independently of one another hydrogen atom or methyl.

In general, the meaning of any group, residue, heteroatom, number etc. which can occur more than once in the compounds of the formula I, is independent of the meaning of this group, residue, heteroatom, number etc. in any other occurrence. All groups, residues, heteroatoms, numbers etc. which can occur more than once in the compounds of the formula I can be identical or different.

As used herein, the term alkyl is to be understood in the broadest sense to mean hydrocarbon residues which can be linear, i.e. straight-chain, or branched and which can be acyclic or cyclic residues or comprise any combination of acyclic and cyclic subunits. Further, the term alkyl as used herein expressly includes saturated groups as well as unsaturated groups which latter groups contain one or more, for example one, two or three, double bonds and/or triple bonds, provided that the double bonds are not located within a cyclic alkyl group in such a manner that an aromatic system results. All these statements also apply if an alkyl group occurs as a substituent on another residue, for example in an alkyloxy residue, an alkyloxycarbonyl residue or an arylalkyl residue. Examples of alkyl residues containing 1, 2, 3, 4, 5, 6, 7 or 8 carbon atoms are methyl, ethyl, propyl, butyl, pentyl, hexyl, heptyl or octyl, the n-isomers of all these residues, isopropyl, isobutyl, 1-methylbutyl, isopentyl, neopentyl, 2,2-dimethylbutyl, 2-methylpentyl, 3-methylpentyl, isohexyl, sec-butyl, tert-butyl, tert-pentyl, sec-butyl, tert-butyl or tert-pentyl.

Unsaturated alkyl residues are, for example, alkenyl residues such as vinyl, 1-propenyl, 2-propenyl (=allyl), 2-butenyl, 3-butenyl, 2-methyl-2-butenyl, 3-methyl-2-butenyl, 5-hexenyl or 1,3-pentadienyl, or alkynyl residues such as ethynyl, 1-propynyl, 2-propynyl (=propargyl) or 2-butynyl. Alkyl residues can also be unsaturated when they are substituted.

Examples of cyclic alkyl residues are cycloalkyl residues containing 3, 4, 5 or 6 ring carbon atoms like cyclopropyl, cyclobutyl, cyclopentyl or cyclohexyl, which can also be substituted and/or unsaturated. Unsaturated cyclic alkyl groups and unsaturated cycloalkyl groups like, for example, cyclopentenyl or cyclohexenyl can be bonded via any carbon atom.

Of course, a cyclic alkyl group has to contain at least three carbon atoms, and an unsaturated alkyl group has to contain at least two carbon atoms. Thus, a group like $(C_1-C_8)$-alkyl is to be understood as comprising, among others, saturated acyclic $(C_1-C_8)$-alkyl, $(C_3-C_6)$-cycloalkyl, and unsaturated $(C_2-C_8)$-alkyl like $(C_2-C_8)$-alkenyl or $(C_2-C_8)$-alkynyl. Similarly, a group like $(C_1-C_4)$-alkyl is to be understood as comprising, among others, saturated acyclic $(C_1-C_4)$-alkyl, and unsaturated $(C_2-C_4)$-alkyl like $(C_2-C_4)$-alkenyl or $(C_2-C_4)$-alkynyl.

Unless stated otherwise, the term alkyl preferably comprises acyclic saturated hydro-carbon residues which have from one to six carbon atoms and which can be linear or branched. A particular group of saturated acyclic alkyl residues is formed by $(C_1-C_4)$-alkyl residues like methyl, ethyl, n-propyl, isopropyl, n-butyl, isobutyl, sec-butyl and tert-butyl.

Unless stated otherwise, and irrespective of any specific substituents bonded to alkyl groups which are indicated in the definition of the compounds of the formula I, alkyl groups can in general be unsubstituted or substituted by one or more, for example one, two or three, identical or different substituents. Any kind of substituents present in substituted alkyl residues can be present in any desired position provided that the substitution does not lead to an unstable molecule. Examples of substituted alkyl residues are alkyl residues in which one or more, for example 1, 2 or 3, hydrogen atoms are replaced with halogen atoms, in particular fluorine atoms.

The term mono- or bicyclic 5- to 10-membered carbocyclic aryl group refers to for example phenyl or napthyl.

The term mono- or bicyclic 5- to 10-membered heteroaryl containing one or two nitrogen atoms as ring heteroatoms refers to ($C_5$-$C_{10}$)-aryl in which one or more of the 5 to 10 ring carbon atoms are replaced by heteroatoms such as nitrogen, oxygen or sulfur. Examples are pyridyl; such as 2-pyridyl, 3-pyridyl or 4-pyridyl; pyrrolyl; such as 2-pyrrolyl and 3-pyrrolyl; furyl; such as 2-furyl and 3-furyl; thienyl; such as 2-thienyl and 3-thienyl; imidazolyl, pyrazolyl, oxazolyl, isoxazolyl, thiazolyl, isothiazolyl, tetrazolyl, pyridazinyl, pyrazinyl, pyrimidinyl, indolyl, isoindolyl, indazolyl, phthalazinyl, quinolyl, isoquinolyl or quinoxalinyl.

The term $R^{11}$ and $R^{12}$ together with the nitrogen atom to which they are bonded form a saturated or unsaturated 5- to 6-membered monocyclic heterocyclic ring refers to pyrrol, piperidin, pyrrolidine, morpholine, piperazine, pyridine, pyrimidine, imidazole or thiomorpholine.

The term aryl refers to a monocyclic or polycyclic hydrocarbon residue in which at least one carbocyclic ring is present that has a conjugated pi electron system. In a ($C_6$-$C_{14}$)-aryl residue from 6 to 14 ring carbon atoms are present. Examples of ($C_6$-$C_{14}$)-aryl residues are phenyl, naphthyl, biphenylyl, fluorenyl or anthracenyl. Unless stated otherwise, and irrespective of any specific substituents bonded to aryl groups which are indicated in the definition of the compounds of the formula I, aryl residues, for example phenyl, naphthyl or fluorenyl, can in general be unsubstituted or substituted by one or more, for example one, two or three, identical or different substituents. Aryl residues can be bonded via any desired position, and in substituted aryl residues the substituents can be located in any desired position.

Unless stated otherwise, and irrespective of any specific substituents bonded to aryl groups which are indicated in the definition of the compounds of the formula I, substituents that can be present in substituted aryl groups are, for example, ($C_1$-$C_8$)-alkyl, in particular ($C_1$-$C_4$)-alkyl, such as methyl, ethyl or tert-butyl, hydroxy, ($C_1$-$C_8$)-alkyloxy, in particular ($C_1$-$C_4$)-alkyloxy, such as methoxy, ethoxy or tert-butoxy, methylenedioxy, ethylenedioxy, F, Cl, Br, I, cyano, nitro, trifluoromethyl, trifluoromethoxy, hydroxymethyl, formyl, acetyl, amino, mono- or di-($C_1$-$C_4$)-alkylamino, (($C_1$-$C_4$)-alkyl)carbonylamino like acetylamino, hydroxycarbonyl, (($C_1$-$C_4$)-alkyloxy)carbonyl, carbamoyl, benzyl optionally substituted in the phenyl group, optionally substituted phenyl, optionally substituted phenoxy or benzyloxy optionally substituted in the phenyl group. A substituted aryl group which is present in a specific position of the compounds of formula I can independently of other aryl groups be substituted by substituents selected from any desired subgroup of the substituents listed before and/or in the specific definition of that group. For example, a substituted aryl group may be substituted by one or more identical or different substituents chosen from ($C_1$-$C_4$)-alkyl, hydroxy, ($C_1$-$C_4$)-alkyloxy, F, Cl, Br, I, cyano, nitro, trifluoromethyl, amino, phenyl, benzyl, phenoxy and benzyloxy. In general, preferably not more than two nitro groups are present in the compounds of the formula I.

In monosubstituted phenyl residues the substituent can be located in the 2-position, the 3-position or the 4-position, with the 3-position and the 4-position being preferred. If a phenyl group carries two substituents, they can be located in 2,3-position, 2,4-position, 2,5-position, 2,6-position, 3,4-position or 3,5-position. In phenyl residues carrying three substituents the substituents can be located in 2,3,4-position, 2,3,5-position, 2,3,6-position, 2,4,5-position, 2,4,6-position, or 3,4,5-position. Naphthyl residues can be 1-naphthyl and 2-naphthyl. In substituted naphthyl residues the substituents can be located in any positions, for example in monosubstituted 1-naphthyl residues in the 2-, 3-, 4-, 5-, 6-, 7-, or 8-position and in monosubstituted 2-naphthyl residues in the 1-, 3-, 4-, 5-, 6-, 7-, or 8-position. Biphenylyl residues can be 2-biphenylyl, 3-biphenylyl and 4-biphenylyl. Fluorenyl residues can be 1-, 2-, 3-, 4- or 9-fluorenyl. In monosubstituted fluorenyl residues bonded via the 9-position the substituent is preferably present in the 1-, 2-, 3- or 4-position.

The group Het comprises groups containing 5, 6, 7, 8, 9 or 10 ring atoms in the parent monocyclic or bicyclic heterocyclic ring system. In monocyclic groups Het the heterocyclic ring preferably is a 5-membered, 6-membered or 7-membered ring, particularly preferably a 5-membered or 6-membered ring. In bicyclic groups Het preferably two fused rings are present one of which is a 5-membered ring or 6-membered heterocyclic ring and the other of which is a 5-membered or 6-membered heterocyclic or carbocyclic ring, i.e. a bicyclic ring Het preferably contains 8, 9 or 10 ring atoms, particularly preferably 9 or 10 ring atoms.

Het comprises saturated heterocyclic ring systems which do not contain any double bonds within the rings, as well as mono-unsaturated and poly-unsaturated heterocyclic ring systems which contain one or more, for example one, two, three, four or five, double bonds within the rings provided that the resulting system is stable. Unsaturated rings may be non-aromatic or aromatic, i.e. double bonds within the rings in the group Het may be arranged in such a manner that a conjugated pi electron system results. Aromatic rings in a group Het may be 5-membered or 6-membered rings, i. e. aromatic groups in a group Het contain 5 to 10 ring atoms. Aromatic rings in a group Het thus comprise 5-membered and 6-membered monocyclic heterocycles and bicyclic heterocycles composed of two 5-membered rings, one 5-membered ring and one 6-membered ring, or two 6-membered rings. In bicyclic aromatic groups in a group Het one or both rings may contain heteroatoms. Aromatic groups Het may also be referred to by the customary term heteroaryl for which all the definitions and explanations above and below relating to Het correspondingly apply.

Unless stated otherwise, in the groups Het and any other heterocyclic groups preferably 1, 2, 3 or 4 identical or different ring heteroatoms chosen from nitrogen, oxygen and sulfur are present. Particularly preferably in these groups one or two identical or different heteroatoms chosen from nitrogen, oxygen and sulfur are present. The ring heteroatoms can be present in any desired number and in any position with respect to each other provided that the resulting heterocyclic system is known in the art and is stable and suitable as a subgroup in a drug substance. Examples of parent structures of heterocycles from which the group Het can be derived are aziridine, oxirane, azetidine, pyrrole, furan, thiophene, dioxole, imidazole, pyrazole, oxazole, isoxazole, thiazole, isothiazole, 1,2,3-triazole, 1,2,4-triazole, tetrazole, pyridine, pyran, thiopyran, pyridazine, pyrimidine, pyrazine, 1,2-oxazine, 1,3-oxazine, 1,4-oxazine, 1,2-thiazine, 1,3-thiazine, 1,4-thiazine, 1,2,3-triazine, 1,2,4-triazine, 1,3,5-triazine, azepine, 1,2-diazepine, 1,3-diazepine, 1,4-diazepine, indole, isoindole, benzofuran, benzothiophene, 1,3-benzodioxole, indazole, benzimidazole, benzoxazole, benzothiazole, quinoline, isoquinoline, chromane, isochromane, cinnoline, quinazoline, quinoxaline, phthalazine, pyridoimidazoles, pyridopyridines, pyridopyrimidines, purine, pteridine etc. as well as ring systems which result from the listed heterocycles by fusion (or condensation) of a carbocyclic ring, for example benzo-fused, cyclopenta-fused, cyclohexa-fused or cyclohepta-fused derivatives of these heterocycles.

The fact that many of the before-listed names of heterocycles are the chemical names of unsaturated or aromatic ring systems does not imply that the groups Het could only be derived from the respective unsaturated ring system. The names here only serve to describe the ring system with respect to ring size and the number of the heteroatoms and their relative positions. As explained above, the group Het can be saturated or partially unsaturated or aromatic, and can thus be derived not only from the before-listed heterocycles themselves but also from all their partially or completely hydrogenated analogues and also from their more highly unsaturated analogues if applicable. As examples of completely or partially hydrogenated analogues of the before-listed heterocycles from which the groups Het may be derived the following may be mentioned: pyrroline, pyrrolidine, tetrahydrofuran, tetrahydrothiophene, dihydropyridine, tetrahydropyridine, piperidine, 1,3-dioxolane, 2-imidazoline, imidazolidine, 4,5-dihydro-1,3-oxazol, 1,3-oxazolidine, 4,5-dihydro-1,3-thiazole, 1,3-thiazolidine, perhydro-1,4-dioxane, piperazine, perhydro-1,4-oxazine (=morpholine), perhydro-1,4-thiazine (=thiomorpholine), perhydroazepine, indoline, isoindoline, 1,2,3,4-tetrahydroquinoline, 1,2,3,4-tetrahydroisoquinoline, etc.

The residue Het may be bonded via any ring carbon atom, and in the case of nitrogen heterocycles via any suitable ring nitrogen atom. Thus, for example, a pyrrolyl residue can be 1-pyrrolyl, 2-pyrrolyl or 3-pyrrolyl, a pyrrolidinyl residue can be pyrrolidin-1-yl (=pyrrolidino), pyrrolidin-2-yl or pyrrolidin-3-yl, a pyridinyl residue can be pyridin-2-yl, pyridin-3-yl or pyridin-4-yl, a piperidinyl residue can be piperidin-1-yl (=piperidino), piperidin-2-yl, piperidin-3-yl or piperidin-4-yl. Furyl can be 2-furyl or 3-furyl, thienyl can be 2-thienyl or 3-thienyl, imidazolyl can be imidazol-1-yl, imidazol-2-yl, imidazol-4-yl or imidazol-5-yl, 1,3-oxazolyl can be 1,3-oxazol-2-yl, 1,3-oxazol-4-yl or 1,3-oxazol-5-yl, 1,3-thiazolyl can be 1,3-thiazol-2-yl, 1,3-thiazol-4-yl or 1,3-thiazol-5-yl, pyrimidinyl can be pyrimidin-2-yl, pyrimidin-4-yl (=6-pyrimidinyl) or 5-pyrimidinyl, piperazinyl can be piperazin-1-yl (=piperazin-4-yl =piperazino) or piperazin-2-yl. Indolyl can be indol-1-yl, indol-2-yl, indol-3-yl, indol-4-yl, indol-5-yl, indol-6-yl or indol-7-yl. Similarly benzimidazolyl, benzoxazolyl and benzothiazol residues can be bonded via the 2-position and via any of the positions 4, 5, 6, and 7. Quinolinyl can be quinolin-2-yl, quinolin-3-yl, quinolin-4-yl, quinolin-5-yl, quinolin-6-yl, quinolin-7-yl or quinolin-8-yl, isoqinolinyl can be isoquinol-1-yl, isoquinolin-3-yl, isoquinolin-4-yl, isoquinolin-5-yl, isoquinolin-6-yl, isoquinolin-7-yl or isoquinolin-8-yl. In addition to being bonded via any of the positions indicated for quinolinyl and isoquinolinyl, 1,2,3,4-tetrahydroquinolinyl and 1,2,3,4-tetrahydroisoquinolinyl can also be bonded via the nitrogen atoms in 1-position and 2-position, respectively.

Unless stated otherwise, and irrespective of any specific substituents bonded to groups Het or any other heterocyclic groups which are indicated in the definition of the compounds of the formula I, the group Het can be unsubstituted or substituted on ring carbon atoms with one or more, for example one, two, three, four or five, identical or different substituents like $(C_1-C_8)$-alkyl, in particular $(C_1-C_4)$-alkyl, $(C_1-C_8)$-alkyloxy, in particular $(C_1-C_4)$-alkyloxy, $(C_1-C_4)$-alkylthio, halogen, nitro, amino, $((C_1-C_4)$-alkyl)carbonylamino like acetylamino, trifluoromethyl, trifluoromethoxy, hydroxy, oxo, hydroxy-$(C_1-C_4)$-alkyl such as, for example, hydroxymethyl or 1-hydroxyethyl or 2-hydroxyethyl, methylenedioxy, ethylenedioxy, formyl, acetyl, cyano, aminosulfonyl, methylsulfonyl, hydroxycarbonyl, aminocarbonyl, $(C_1-C_4)$-alkyloxycarbonyl, optionally substituted phenyl, optionally substituted phenoxy, benzyl optionally substituted in the phenyl group, benzyloxy optionally substituted in the phenyl group, etc. The substituents can be present in any desired position provided that a stable molecule results. Of course an oxo group cannot be present in an aromatic ring. Each suitable ring nitrogen atom in a group Het can independently of each other be unsubstituted, i. e. carry a hydrogen atom, or can be substituted, i.e. carry a substituent like $(C_1-C_8)$-alkyl, for example $(C_1-C_4)$-alkyl such as methyl or ethyl, optionally substituted phenyl, phenyl-$(C_1-C_4)$-alkyl, for example benzyl, optionally substituted in the phenyl group, hydroxy-$(C_2-C_4)$-alkyl such as, for example 2-hydroxyethyl, acetyl or another acyl group, methylsulfonyl or another sulfonyl group, aminocarbonyl, $(C_1-C_4)$-alkyloxycarbonyl, etc. In general, in the compounds of the formula I nitrogen heterocycles can also be present as N-oxides or as quaternary salts. Ring sulfur atoms can be oxidized to the sulfoxide or to the sulfone. Thus, for example a tetrahydrothienyl residue may be present as S,S-dioxotetrahydrothienyl residue or a thiomorpholinyl residue like thiomorpholin-4-yl may be present as 1-oxo-thiomorpholin-4-yl or 1,1-dioxo-thiomorpholin-4-yl. A substituted group Het that can be present in a specific position of the compounds of formula I can independently of other groups Het be substituted by substituents selected from any desired subgroup of the substituents listed before and/or in the definition of that group.

Halogen is fluorine, chlorine, bromine or iodine, preferably fluorine, chlorine or bromine, particularly preferably chlorine or bromine.

Optically active carbon atoms present in the compounds of the formula I can independently of each other have R configuration or S configuration. The compounds of the formula I can be present in the form of pure enantiomers or pure diastereomers or in the form of mixtures of enantiomers and/or diastereomers, for example in the form of racemates. The present invention relates to pure enantiomers and mixtures of enantiomers as well as to pure diastereomers and mixtures of diastereomers. The invention comprises mixtures of two or of more than two stereoisomers of the formula I, and it comprises all ratios of the stereoisomers in the mixtures. In case the compounds of the formula I can be present as E isomers or Z isomers (or cis isomers or trans isomers) the invention relates both to pure E isomers and pure Z isomers and to E/Z mixtures in all ratios. The invention also comprises all tautomeric forms of the compounds of the formula I.

Diastereomers, including E/Z isomers, can be separated into the individual isomers, for example, by chromatography. Racemates can be separated into the two enantiomers by customary methods, for example by chromatography on chiral phases or by resolution, for example by crystallization of diastereomeric salts obtained with optically active acids or bases. Stereochemically uniform compounds of the formula I can also be obtained by employing stereochemically uniform starting materials or by using stereoselective reactions.

The choice of incorporating into a compound of the formula I a building block with R configuration or S configuration, or in the case of an amino acid unit present in a compound of the formula I of incorporating a building block designated as D-amino acid or L-amino acid, can depend, for example, on the desired characteristics of the compound of the formula I. For example, the incorporation of a D-amino acid building block can confer increased stability in vitro or in vivo. The incorporation of a D-amino acid building block also can achieve a desired increase or decrease in the pharmacological activity of the compound. In some cases it can be desirable to allow the compound to remain active for only a short period of time. In such cases, the incorporation of an L-amino acid building block in the compound can allow endogenous peptidases in an individual to digest the compound in vivo, thereby limiting the individual's exposure to the active compound. A similar effect may also be observed in the compounds of the invention by changing the configuration in another building block from S configuration to R configuration or vice versa. By taking into consideration the medical needs one skilled in the art can determine the desirable characteristics, for example a favorable stereochemistry, of the required compound of the invention.

Physiologically tolerable salts of the compounds of formula I are nontoxic salts that are physiologically acceptable, in particular pharmaceutically utilizable salts. Such salts of compounds of the formula I containing acidic groups, for example a carboxy group COOH, are for example alkali metal salts or alkaline earth metal salts such as sodium salts, potassium salts, magnesium salts and calcium salts, and also salts with physiologically tolerable quarternary ammonium ions such as tetramethylammonium or tetraethylammonium, and acid addition salts with ammonia and physiologically tolerable organic amines, such as methylamine, dimethylamine, trimethylamine, ethylamine, triethylamine, ethanolamine or tris-(2-hydroxyethyl)amine. Basic groups contained in the compounds of the formula I, for example amino groups or guanidino groups, form acid addition salts, for example with inorganic acids such as hydrochloric acid, hydrobromic acid, sulfuric acid, nitric acid or phosphoric acid, or with organic carboxylic acids and sulfonic acids such as formic acid, acetic acid, oxalic acid, citric acid, lactic acid, malic acid, succinic acid, malonic acid, benzoic acid, maleic acid, fumaric acid, tartaric acid, methanesulfonic acid or p-toluenesulfonic acid. Compounds of the formula I which simultaneously contain a basic group and an acidic group, for example a guanidino group and a carboxy group, can also be present as zwitterions (betaines) which are likewise included in the present invention.

Salts of compounds of the formula I can be obtained by customary methods known to those skilled in the art, for example by combining a compound of the formula I with an inorganic or organic acid or base in a solvent or dispersant, or from other salts by cation exchange or anion exchange. The present invention also includes all salts of the compounds of the formula I which, because of low physiologically tolerability, are not directly suitable for use in pharmaceuticals but are suitable, for example, as intermediates for carrying out further chemical modifications of the compounds of the formula I or as starting materials for the preparation of physiologically tolerable salts. The present invention furthermore includes all solvates of compounds of the formula I, for example hydrates or adducts with alcohols.

The invention also includes derivatives and modifications of the compounds of the formula I, for example prodrugs, protected forms and other physiologically tolerable derivatives, as well as active metabolites of the compounds of the formula I. The invention relates in particular to prodrugs and protected forms of the compounds of the formula I which can be converted into compounds of the formula I under physiological conditions. Suitable prodrugs for the compounds of the formula I, i.e. chemically modified derivatives of the compounds of the formula I having properties which are improved in a desired manner, for example with respect to solubility, bioavailability or duration of action, are known to those skilled in the art. More detailed information relating to prodrugs is found in standard literature like, for example, Design of Prodrugs, H. Bundgaard (ed.), Elsevier, 1985; Fleisher et al., Advanced Drug Delivery Reviews 19 (1996) 115-130; or H. Bundgaard, Drugs of the Future 16 (1991) 443 which are all incorporated herein by reference. Suitable prodrugs for the compounds of the formula I are especially acyl prodrugs and carbamate prodrugs of acylatable nitrogen-containing groups such as amino groups and the guanidino group and also ester prodrugs and amide prodrugs of carboxylic acid groups which may be present in compounds of the formula I. In the acyl prodrugs and carbamate prodrugs one or more, for example one or two, hydrogen atoms on nitrogen atoms in such groups are replaced with an acyl group or a carbamate, preferably a $(C_1-C_6)$-alkyloxycarbonyl group. Suitable acyl groups and carbamate groups for acyl prodrugs and carbamate prodrugs are, for example, the groups $R^{p1}$—CO— and $R^{p2}O$—CO—, in which $R^{p1}$ is hydrogen, $(C_1-C_{18})$-alkyl, $(C_3-C_8)$-cycloalkyl, $(C_3-C_8)$-cycloalkyl-$(C_1-C_4)$-alkyl-, $(C_6-C_{14})$-aryl, Het-, $(C_6-C_{14})$-aryl-$(C_1-C_4)$-alkyl- or Het-$(C_1-C_4)$-alkyl- and in which $R^{p2}$ has the meanings indicated for $R^{p1}$ with the exception of hydrogen.

A further embodiment of the present invention are prodrugs of the compounds of the formula I, preferably $(C_1-C_6)$-acyl prodrugs and $(C_1-C_6)$-alkyloxycarbonyl prodrugs.

The present invention also relates to processes of preparation by which the compounds of the formula I are obtainable and which comprise carrying out one or more of the synthesis steps described below. The compounds of the formula I can generally be prepared, for example in the course of a convergent synthesis, by linkage of two or more fragments which can be derived retrosynthetically from the formula I. In the course of the preparation of the compounds of the formula I it can generally be advantageous or necessary to introduce functional groups which could lead to undesired reactions or side reactions in the respective synthesis step, in the form of precursor groups which are later converted into the desired functional groups, or to temporarily block functional groups by a protective group strategy suited to the synthesis problem. Such strategies are well known to those skilled in the art (see, for example, Greene and Wuts, Protective Groups in Organic Synthesis, Wiley, 1991). As examples of precursor groups nitro groups and cyano groups may be mentioned which can later be converted by reduction, for example by catalytic hydrogenation, into amino groups and aminomethyl groups, respectively. Protective groups can also have the meaning of a solid phase, and cleavage from the solid phase stands for the removal of the protective group. The use of such techniques is known to those skilled in the art (Burgess K (Ed.) Solid Phase Organic Synthesis, New York: Wiley, 2000). For example, a phenolic hydroxy group can be attached to a trityl-polystyrene resin, which serves as a protecting group, and the molecule is cleaved from this resin by treatment with TFA at a later stage iof the synthesis.

For example, for the preparation of a compound of the formula I a building block of the formula XI,

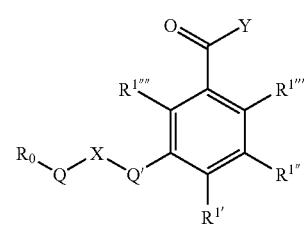

XI in which $R_0$, Q, Q', X, are as defined above for the compounds of the formula I but functional groups can optionally also be present in the form of precursor groups or can be protected by protective groups known to those skilled in the art, e.g. an amino group can be protected with a tert.-butyloxycarbonyl group or a benzyloxycarbonyl group. $R^{1\prime}$, $R^{1\prime\prime\prime}$, $R^{1\prime\prime\prime\prime}$, $R^{1\prime\prime\prime\prime\prime}$, are defined as hydrogen or as $R^1$ which has the same meaning as in formula I but can optionally also be present in the form of precursor groups or can be protected by protective groups known to those skilled in the art, e.g. a hydroxy group may be attached to a polystyrene resin, and Y is a nucleophilically substitutable leaving group or a hydroxyl group, is reacted with a fragment of the formula XII

$$H-NR_{10}-V \quad\quad (XII)$$

in which $R_{10}$ and V are as defined above for the compounds of the formula I but functional groups can optionally also be present in the form of precursor groups or can be protected by protective groups.

The group COY in the formula XI is preferably the carboxylic acid group COOH or an activated carboxylic acid derivative. Y can thus be, for example, hydroxyl, halogen, in particular chlorine or bromine, alkoxy, in particular methoxy or ethoxy, aryloxy, for example phenoxy or pentafluorophenoxy, phenylthio, methylthio, 2-pyridylthio or a residue of a nitrogen heterocycle bonded via a nitrogen atom, in particular a residue of an azole, such as, for example, 1-imidazolyl. Y can furthermore be, for example, $((C_1-C_4)\text{-alkyl})-O-CO-O-$ or tolylsulfonyloxy and the activated acid derivative can thus be a mixed anhydride.

If Y is hydroxyl, then the carboxylic acid is expediently first activated, for example by one of the various methods used for peptide couplings which are well known to those skilled in the art. Examples of suitable activation agents are O-((cyano(ethoxycarbonyl) methylene)amino)-1,1,3,3-tetramethyluronium tetrafluoroborate (TOTU); (König et al., Proc. 21st Europ. Peptide Symp. 1990 (eds. Giralt, Andreu), Escom, Leiden 1991, p. 143), O-(benzotriazol-1-yl)-1,1,3,3-tetramethyluronium hexafluorophosphate (HBTU), O-(7-azabenzotriazol-1-yl)-1,1,3,3-tetramethyluronium hexafluorophosphate (HATU) (L. A. Carpino, J. Am. Chem. Soc. 1993, 115, 4397), or carbodiimides like dicyclohexylcarbodiimide or diisopropylcarbodiimide. The activation of the carboxylic acid function may also favorably be carried, for example, by conversion of the carboxylic acid group into the pentafluorophenyl ester using dicyclohexylcarbodiimide and pentafluorophenol. A number of suitable methods for the preparation of activated carboxylic acid derivatives are also indicated with details of source literature in J. March, Advanced Organic Chemistry, Fourth Edition, John Wiley & Sons, 1992. The activation and the subsequent reaction with the compound of the formula III are usually carried in the presence of an inert solvent or diluent, for example DCM, chloroform, THF, diethyl ether, n-heptane, n-hexane, n-pentane, cyclohexane, diisopropyl ether, methyl tert-butyl ether, acetonitrile, DMF, DMSO, dioxane, toluene, benzene, ethyl acetate or a mixture of these solvents, if appropriate with addition of a base such as, for example, potassium tert-butoxide or tributylamine or triethylamine or diisopropylethylamine.

The resulting product is a compound of the formula I in which functional groups can also be present in the form of precursor groups or can be protected by protective groups. If still any protective groups or precursor groups are present they are then removed by known methods (see Greene and Wuts, Protective Groups in Organic Synthesis, Wiley, 1991), or converted in the desired final groups, respectively. E.g., if a carboxylic acid group protected as tert-butyl ester and the free carboxylic acid is to be prepared as the final compound the protective group can be removed by reaction with trifluoroacetic acid or tert.-butyloxycarbonyl protecting groups can be removed by treatment with trifluoroacetic acid. If desired, with the obtained compounds further reactions can then be carried out by standard processes, for example acylation reactions or esterification reactions, or the compounds can be converted into physiologically tolerable salts or prodrugs by standard processes known to those skilled in the art.

Other compounds of the formula I can be prepared in a similar fashion as described above by coupling of a fragment of the formula XIII with fragment XII.

$$R_0\text{-Q-X-Q}'\text{-W}-C(O)-Y \quad\quad (XIII)$$

in which $R_0$, Q, Q', X and Y are as defined above for the compounds of the formula I, W is the substructure of formula III, but functional groups can optionally also be present in the form of precursor groups or can be protected by protective groups known to those skilled in the art, e.g. an amino group can be protected with a tert.-butyloxycarbonyl group or a benzyloxycarbonyl group or a hydroxy group may be attached to a polystyrene resin.

The fragments of the formula XI, XII and XIII are prepared by methods well known to those skilled in the art (E.g. in J March, Advanced Organic Chemistry, $4^{th}$ Edition, John Wiley & Sons, 1992; R C Larock, Comprehensive Organic Transformations, VCH Publishers, New York 1989).

The compounds of the present invention are serine protease inhibitors which inhibit the activity of the blood coagulation enzymes factor Xa and/or factor VIIa. In particular, they are highly active inhibitors of factor Xa. They are specific serine protease inhibitors inasmuch as they do not substantially inhibit the activity of other proteases whose inhibition is not desired. The activity of the compounds of the formula I can be determined, for example, in the assays described below or in other assays known to those skilled in the art. With respect to factor Xa inhibition, a preferred embodiment of the invention comprises compounds which have a Ki≦1 for factor Xa inhibition as determined in the assay described below, with or without concomitant factor VIIa inhibition, and which preferably do not substantially inhibit the activity of other proteases involved in coagulation and fibrinolysis whose inhibition is not desired (using the same concentration of the inhibitor). The compounds of the invention inhibit factor Xa catalytic activity either directly, within the prothrombinase complex or as a soluble subunit, or indirectly, by inhibiting the assembly of factor Xa into the prothrombinase complex.

The present invention also relates to the compounds of the formula I and/or their physiologically tolerable salts and/or their prodrugs for use as pharmaceuticals (or medicaments), to the use of the compounds of the formula I and/or their physiologically tolerable salts and/or their prodrugs for the production of pharmaceuticals for inhibition of factor Xa and/or factor VIIa or for influencing blood coagulation, inflammatory response or fibrinolysis or for the therapy or prophylaxis of the diseases mentioned above or below, for example for the production of pharmaceuticals for the therapy and prophylaxis of cardiovascular disorders, thromboembolic diseases or restenoses. The invention also relates to the use of the compounds of the formula I and/or their physiologically tolerable salts and/or their prodrugs for the inhibition of factor Xa and/or factor VIIa or for influencing blood coagulation or fibrinolysis or for the therapy or prophylaxis of the diseases mentioned above or below, for example for use in the therapy and prophylaxis of cardiovascular disorders, thromboembolic diseases or restenoses, and to methods of treatment aiming at such purposes including methods for said therapies and prophylaxis. The present invention also relates to pharmaceutical preparations (or pharmaceutical compositions) which contain an effective amount of at least one compound of the formula I and/or its physiologically tolerable salts and/or its prodrugs in addition to a customary pharmaceutically acceptable carrier, i. e. one or more pharmaceutically acceptable carrier substances or excipients and/or auxiliary substances or additives.

Preferred are the treatment of disease states such as abnormal thrombus formation, acute myocardial infarction, unstable angina, thromboembolism, acute vessel closure associated with thrombolytic therapy or percutaneous transluminal coronary angioplasty, transient ischemic attacks, stroke, pathologic thrombus formation occuring in the veins of the lower extremities following abdominal, knee and hip surgery, a risk of pulmonary thromboembolism, or disseminated systemic intravascular coagulatopathy ocurring in vascular systems during septic shock, certain viral infections or cancer.

The compounds of the formula I and their physiologically tolerable salts and their prodrugs can be administered to animals, preferably to mammals, and in particular to humans as pharmaceuticals for therapy or prophylaxis. They can be administered on their own, or in mixtures with one another or in the form of pharmaceutical preparations which permit enteral or parenteral administration.

The pharmaceuticals can be administered orally, for example in the form of pills, tablets, lacquered tablets, coated tablets, granules, hard and soft gelatin capsules, solutions, syrups, emulsions, suspensions or aerosol mixtures. Administration, however, can also be carried out rectally, for example in the form of suppositories, or parenterally, for example intravenously, intramuscularly or subcutaneously, in the form of injection solutions or infusion solutions, microcapsules, implants or rods, or percutaneously or topically, for example in the form of ointments, solutions or tinctures, or in other ways, for example in the form of aerosols or nasal sprays.

The pharmaceutical preparations according to the invention are prepared in a manner known per se and familiar to one skilled in the art, pharmaceutically acceptable inert inorganic and/or organic carriers being used in addition to the compound(s) of the formula I and/or its (their) physiologically tolerable salts and/or its (their) prodrugs. For the production of pills, tablets, coated tablets and hard gelatin capsules it is possible to use, for example, lactose, corn starch or derivatives thereof, talc, stearic acid or its salts, etc. Carriers for soft gelatin capsules and suppositories are, for example, fats, waxes, semisolid and liquid polyols, natural or hardened oils, etc. Suitable carriers for the production of solutions, for example injection solutions, or of emulsions or syrups are, for example, water, saline, alcohols, glycerol, polyols, sucrose, invert sugar, glucose, vegetable oils, etc. Suitable carriers for microcapsules, implants or rods are, for example, copolymers of glycolic acid and lactic acid. The pharmaceutical preparations normally contain about 0.5% to 90% by weight of the compounds of the formula I and/or their physiologically tolerable salts and/or their prodrugs. The amount of the active ingredient of the formula I and/or its physiologically tolerable salts and/or its prodrugs in the pharmaceutical preparations normally is from about 0.5 mg to about 1000 mg, preferably from about 1 mg to about 500 mg.

In addition to the active ingredients of the formula I and/or their physiologically acceptable salts and/or prodrugs and to carrier substances, the pharmaceutical preparations can contain additives such as, for example, fillers, disintegrants, binders, lubricants, wetting agents, stabilizers, emulsifiers, preservatives, sweeteners, colorants, flavorings, aromatizers, thickeners, diluents, buffer substances, solvents, solubilizers, agents for achieving a depot effect, salts for altering the osmotic pressure, coating agents or antioxidants. They can also contain two or more compounds of the formula I and/or their physiologically tolerable salts and/or their prodrugs. In case a pharmaceutical preparation contains two or more compounds of the formula I the selection of the individual compounds can aim at a specific overall pharmacological profile of the pharmaceutical preparation. For example, a highly potent compound with a shorter duration of action may be combined with a long-acting compound of lower potency. The flexibility permitted with respect to the choice of substituents in the compounds of the formula I allows a great deal of control over the biological and physico-chemical properties of the compounds and thus allows the selection of such desired compounds. Furthermore, in addition to at least one compound of the formula I and/or its physiologically tolerable salts and/or its prodrugs, the pharmaceutical preparations can also contain one or more other therapeutically or prophylactically active ingredients.

As inhibitors of factor Xa and/or factor VIIa the compounds of the formula I and their physiologically tolerable salts and their prodrugs are generally suitable for the therapy and prophylaxis of conditions in which the activity of factor Xa and/or factor VIIa plays a role or has an undesired extent, or which can favorably be influenced by inhibiting factor Xa and/or factor VIIa or decreasing their activities, or for the prevention, alleviation or cure of which an inhibition of factor Xa and/or factor VIIa or a decrease in their activity is desired by the physician. As inhibition of factor Xa and/or factor VIIa influences blood coagulation and fibrinolysis, the compounds of the formula I and their physiologically tolerable salts and their prodrugs are generally suitable for reducing blood clotting, or for the therapy and prophylaxis of conditions in which the activity of the blood coagulation system plays a role or has an undesired extent, or which can favorably be influenced by reducing blood clotting, or for the prevention, alleviation or cure of which a decreased activity of the blood coagulation system is desired by the physician. A specific subject of the present invention thus are the reduction or inhibition of unwanted blood clotting, in particular in an individual, by administering an effective amount of a compound I or a physiologically tolerable salt or a prodrug thereof, as well as pharmaceutical preparations therefor.

Conditions in which a compound of the formula I can be favorably used include, for example, cardiovascular disorders, thromboembolic diseases or complications associated, for example, with infection or surgery. The compounds of the present invention can also be used to reduce an inflammatory response. Examples of specific disorders for the treatment or prophylaxis of which the compounds of the formula I can be used are coronary heart disease, myocardial infarction, angina pectoris, vascular restenosis, for example restenosis following angioplasty like PTCA, adult respiratory disstress syndrome, multi-organ failure, stroke and disseminated intravascular clotting disorder. Examples of related complications associated with surgery are thromboses like deep vein and proximal vein thrombosis which can occur following surgery. In view of their pharmacological activity the compounds of the invention can replace or supplement other anticoagulant agents such as heparin. The use of a compound of the invention can result, for example, in a cost saving as compared to other anticoagulants.

When using the compounds of the formula I the dose can vary within wide limits and, as is customary and is known to the physician, is to be suited to the individual conditions in each individual case. It depends, for example, on the specific compound employed, on the nature and severity of the disease to be treated, on the mode and the schedule of administration, or on whether an acute or chronic condition is treated or whether prophylaxis is carried out. An appropriate dosage can be established using clinical approaches well known in the medical art. In general, the daily dose for achieving the desired results in an adult weighing about 75 kg is from 0.01 mg/kg to 100 mg/kg, preferably from 0.1 mg/kg to 50 mg/kg, in particular from 0.1 mg/kg to 10 mg/kg, (in each case in mg per kg of body weight). The daily dose can be divided, in particular in the case of the administration of relatively large amounts, into several, for example 2, 3 or 4, part administrations. As usual, depending on individual behavior it may be necessary to deviate upwards or downwards from the daily dose indicated.

A compound of the formula I can also advantageously be used as an anticoagulant outside an individual. For example, an effective amount of a compound of the invention can be contacted with a freshly drawn blood sample to prevent coagulation of the blood sample. Further, a compound of the formula I and its salts can be used for diagnostic purposes, for example in in vitro diagnoses, and as an auxiliary in biochemical investigations. For example, a compound of the formula I can be used in an assay to identify the presence of factor Xa and/or factor VIIa or to isolate factor Xa and/or factor VIIa in a substantially purified form. A compound of the invention can be labeled with, for example, a radioisotope, and the labeled compound bound to factor Xa and/or factor VIIa is then detected using a routine method useful for detecting the particular label. Thus, a compound of the formula I or a salt thereof can be used as a probe to detect the location or amount of factor Xa and/or factor VIIa activity in vivo, in vitro or ex vivo.

Furthermore, the compounds of the formula I can be used as synthesis intermediates for the preparation of other compounds, in particular of other pharmaceutical active ingredients, which are obtainable from the compounds of the formula I, for example by introduction of substituents or modification of functional groups.

It is understood that changes that do not substantially affect the activity of the various embodiments of this invention are included within the invention disclosed herein. Thus, the following examples are intended to illustrate but not limit the present invention.

EXAMPLES

Abbreviations Used:

| tert-Butyl | tBu |
| Dichloromethane | DCM |
| Diethyl azodicarboxylate | DEAD |
| Diisopropyl azodicarboxylate | DIAD |
| N,N'-Diisopropylcarbodiimide | DIC |
| N,N-Diisopropyl-N-ethylamine | DIEA |
| N,N-Dimethylformamide | DMF |
| Dimethylsulfoxide | DMSO |
| O-(7-Azabenzotriazol-1-yl)-N,N,N',N'-tetramethyluronium-hexafluorophosphate | HATU |
| 1-Hydroxy-7-azabenzotriazole | HOAt |
| N-Ethylmorpholine | NEM |
| Methanol | MeOH |
| Tetrahydrofuran | THF |
| Trifluoroacetic acid | TFA |

When in the final step of the synthesis of a compound an acid such as trifluoroacetic acid or acetic acid was used, for example when trifluoroacetic acid was employed to remove a tert-butyl group or when a compound was purified by chromatography using an eluent which contained such an acid, in some cases, depending on the work-up procedure, for example the details of a freeze-drying process, the compound was obtained partially or completely in the form of a salt of the acid used, for example in the form of the acetic acid salt or trifluoroacetic acid salt or hydrochloric acid salt.

Example 1

(S)-(1-Carbamimidoyl-piperidin-4-yl)-{3-[2-(2,4-dichloro-phenyl)-ethoxy]-5-hydroxy-benzoylamino}-acetic acid methyl ester

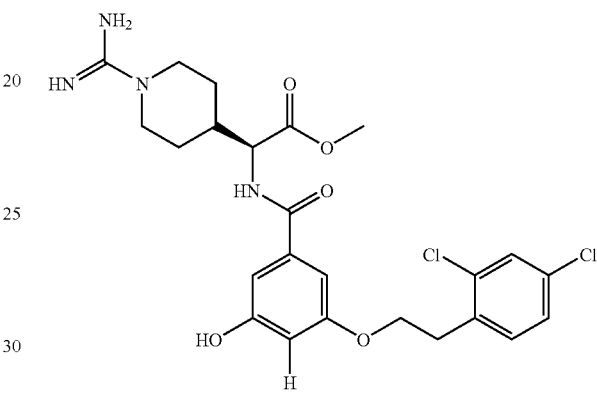

(a) 3,5-Dihydroxy-benzoic acid allyl ester

To 1.5 g of 3,5-dihydroxybenzoic acid in screw-capped vial was added 10 g of allyl alcohol and the vial was closed and cooled to −20° C. To the cold contents of the reaction vial was added 5 mL of trimethylsilyl chloride via syringe through a septum. The reaction vial was allowed to warm to room temperature and agitated for 16 hours. The vial was opened carefully and its contents transferred to a round-bottomed flask. The solvent was removed under reduced pressure and the residual solid was dried under reduced pressure over potassium hydroxide pellets for 12 h. The semisolid product was used in the subsequent synthetic steps without further purification. The product was analyzed by HPLC and had a retention time of 3.65 on 5 cm $C_{18}$ reversed phase column with flow rate of 2.5 mL/min of pure acetonitrile (for solvent A) and 0.1% aqueous trifluroacetic acid (for solvent B). The product was characterized by $^1$H NMR (DMSO-$d_6$, 350 MHz): δ=6.87 (s, 2H, aromatic); 6.44 (s, 1H, aromatic); 5.85-5.96 (m, 1H); 5.16-5.33 (m, 2H); 4.65-4.67(dd, 2H).

(b) 300 mg of (2'-chloro)-Chlorotrityl-polystyrene resin (0.39 mmols; loading 1.3 mmol/g Cl) was treated with 4 mL of dichloroethane and the resin was left to swell at room temperature for 30 minutes. The solvent was removed by filtration and the resin was treated with a solution of 227 mg of 3,5-dihydroxy-benzoic acid allyl ester and 0.4 mL of DIEA in 5 mL anhydrous dichloromethane. The resin suspension was agitated for 3 to 4 h at 60° C. The resin was washed with DMF (3 times), DCM (5 times) and DMF (5 times) and used in next step.

(c) The resin from step (b) was washed with anhydrous THF (3 times) and suspended in 4 mL of anhydrous THF containing 511 mg of triphenylphosphine and 745 mg of 2,4-dichlorophenethyl alcohol. The suspension was cooled to −15° C. and 0.384 mL of DIAD was added. The resin suspension was agitated at room temperature for 12 h. The solvent was removed by filtration and the resin was washed with THF (9 times), DMF (5 times), DCM (5 times). The resin was used in the next step.

(d) The resin from step (c) was suspended in DCM and 365 mg of 1,3-dimethylbarbituric acid was added in the presence of 45 mg of Pd (0)(PPh$_3$)$_4$ under argon. The resin suspension was agitated for one hour at room temperature. The solvent was removed by filtration and the resin was washed with DCM and dried.

(e) Dried resin from step (d) was washed with DMF and suspended in 3 mL DMF containing 265 mg of HOAt and 0.302 mL of DIC. The resin was agitated for 5 minutes and 613 mg of (S)-amino-[1-(tert-butoxycarbonylamino-iminomethyl)-piperidin-4-yl]-acetic acid methyl ester was added. The resin suspension was agitated for 12 h. The resin was washed with DMF and DCM and dried under reduced pressure for 6-8 h.

(f) The dried resin from step (e) was suspended in DCM containing 50% TFA and agitated at room temperature for 45 minutes. The resin suspension was filtered, washed with DCM: TFA (1:1) and the washings combined with the cleavage filtrate. The cleavage solution was dried under reduced pressure. The solid product was lyophilized from 30% aqueous acetonitrile and crude product purified by HPLC on reverse phase C$_{18}$ column. Fractions containing the desired product were pooled and lyophilized to give (S)-(1-Carbamimidoyl-piperidin-4-yl)-{3-[2-(2,4-dichloro-phenyl)-ethoxy]-5-hydroxy-benzoylamino}-acetic acid methyl ester as a white solid. The product was identified by LC/MS to give m/e=523 (M+H)$^+$.

Example 2

4-Bromo-N-(1-carbamimidoyl-piperidin-4-ylmethyl)-3-[2-(2,4-dichloro-phenyl)-ethoxy]-5-hydroxy-benzamide

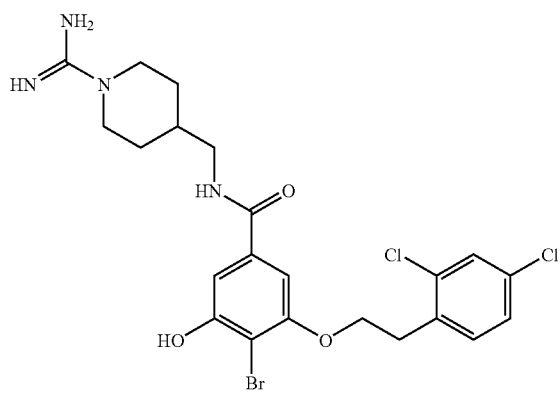

(a) 4-Bromo-3,5-dihydroxy-benzoic acid allyl ester

This compound was prepared analogously to 3,5-Dihydroxy-benzoic acid allyl ester [Example 1(a)], however 4-bromo-3,5-dihydroxybenzoic acid was used instead of 3,5-dihydroxybenzoic acid. $^1$H NMR (DMSO-d$_6$, 350 MHz): δ=7.04 (s, 2H, aromatic); 5.97-6.06 (m, 1H); 5.25-5.40 (m, 2H); 4.73-4.75(dd, 2H).

(b) The title compound was synthesized analogously to Example 1, steps (b)-(f) with the following differences:

In step (b) 4-Bromo-3,5-dihydroxy-benzoic acid allyl ester was used instead of 3,5-dihydroxy-benzoic acid allyl ester;

In step (e) [(4-aminomethyl-piperidin-1-yl)-imino-methyl]-carbamic acid tert-butyl ester was used instead of (S)-amino-[1-(tert-butoxycarbonylamino-imino-methyl)-piperidin-4-yl]-acetic acid methyl ester. The final product was purified by HPLC and characterized by LC/MS to give m/e=543.3 (M+H)$^+$.

Example 3

N-(1-Carbamimidoyl-piperidin-4-ylmethyl)-3-[2-(2,4-dichloro-phenyl)-ethoxy]-5-hydroxy-4-methyl-benzamide

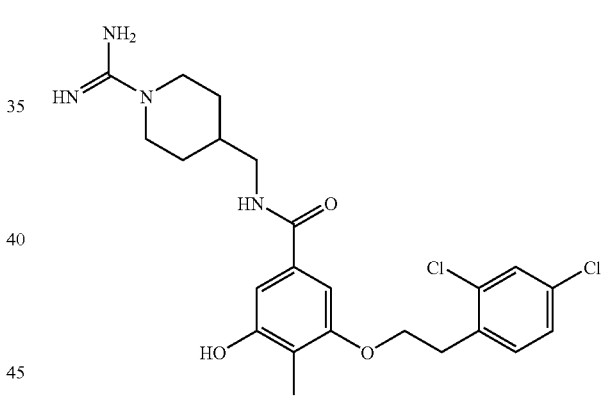

(a) 3,5-dihydroxy-4-methylbenzoic acid allyl ester

This compound was prepared analogously to 3,5-Dihydroxy-benzoic acid allyl ester [Example 1(a)], however 3,5-dihydroxy-4-methylbenzoic acid was used instead of 3,5-dihydroxybenzoic acid.

(b) The title compound was synthesized analogously to Example 2, with the following difference:

3,5-dihydroxy-4-methyl-benzoic acid allyl ester was used instead of 4-Bromo-3,5-dihydroxy-benzoic acid allyl ester. The final product was purified by HPLC and characterized by LC/MS to give m/e=478.8 (M+H)$^+$.

Analogously to the above examples the following example compounds were prepared by similar procedures and characterized by LC/MS:

| Example | Structure | MWt | (M + H)⁺ |
|---|---|---|---|
| 4 | 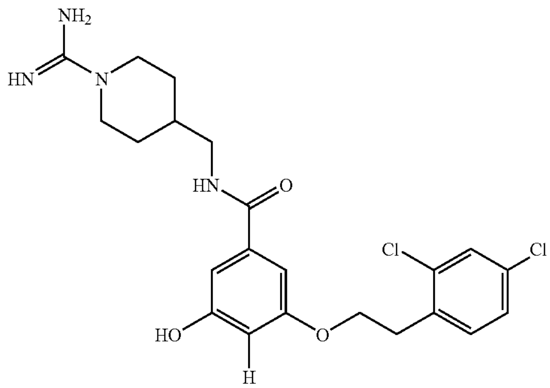 | 464.13 | 465.3 |
| 5 | 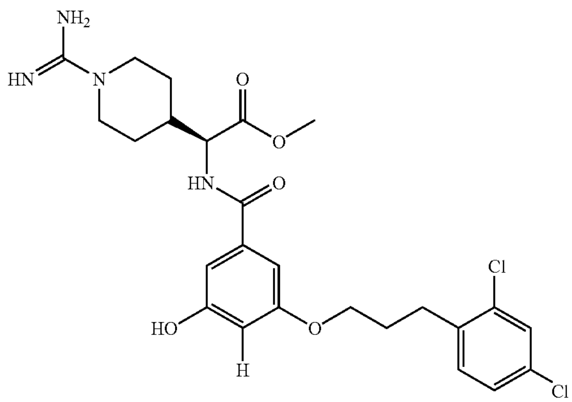 | 536.15 | 537.3 |
| 6 | 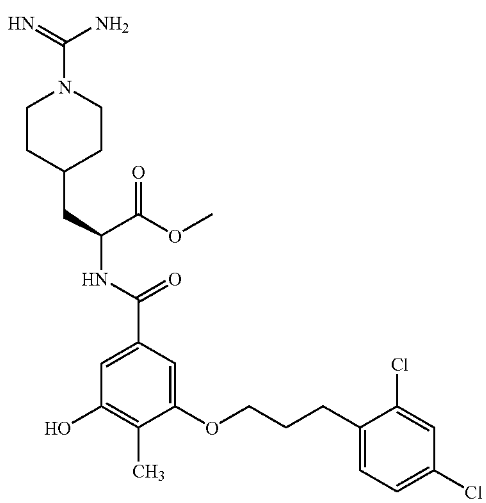 | 564.10 | 565.3 |

-continued

| Example | Structure | MWt | (M + H)⁺ |
|---|---|---|---|
| 7 | 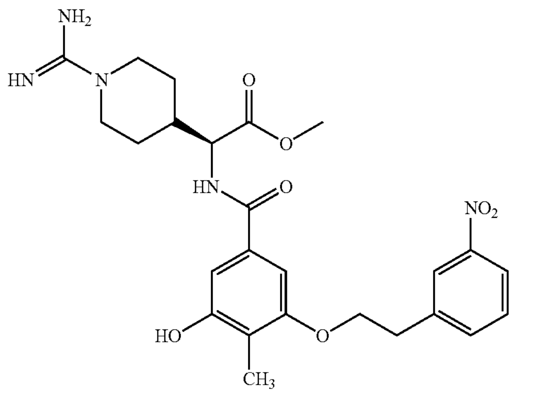 | 513.22 | 514.3 |
| 8 | 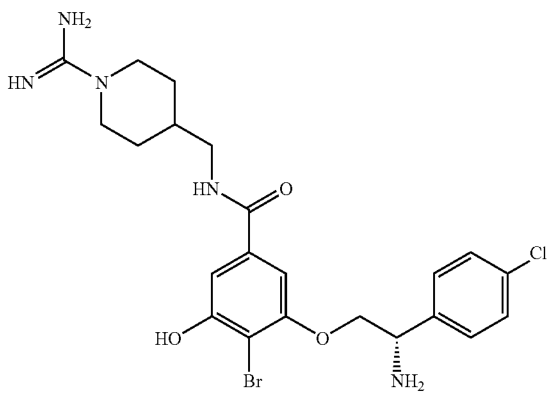 | 523.10 | 524 |
| 9 | 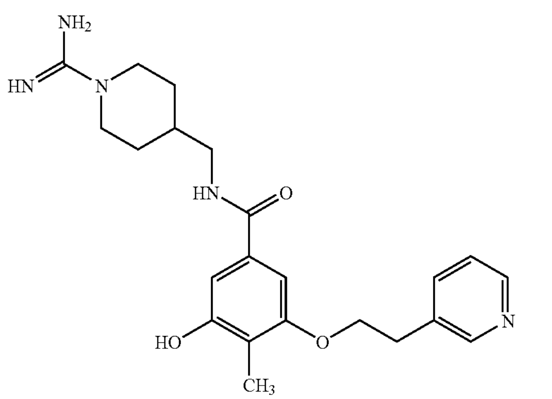 | 411.23 | 412 |
| 10 | 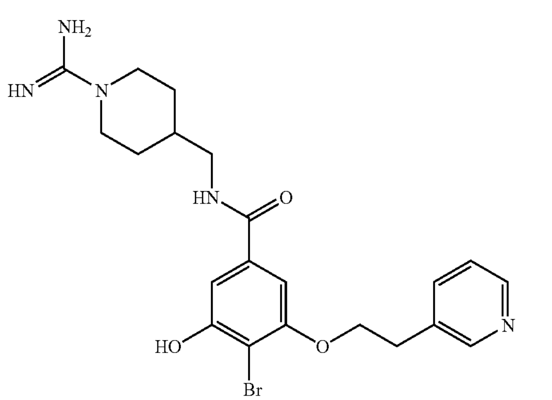 | 475.11 | 476 |

Example 11

N-(1-Carbamimidoyl-piperidin-4-ylmethyl)-3-[2-(2,4-dichloro-phenyl)-ethoxy]-4-methoxy-benzamide

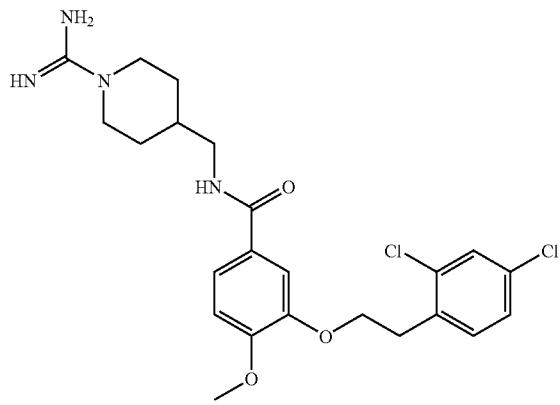

(a) 3-Hydroxy-4-methoxy-benzoic acid methyl ester 10 mL of thionyl chloride was added to 250 mL of methanol at 0° C. The solution was stirred for 10 minutes and 25 g of 3-hydroxy-4-methoxybenzoic acid were added. The reaction was stirred for 16 h at room temperature then heated to 50° C. for 3 h. The solvents were removed under reduced pressure. The residue was used directly in the next step.

(b) 3-[2-(2,4-Dichlorophenyl)-ethoxy]-4-methoxy-benzoic acid methyl ester 20 g of triphenylphosphine and 10 g of 3-Hydroxy-4-methoxy-benzoic acid methyl ester were dissolved in 200 mL of anhydrous THF. The solution was cooled to 0° C. to 10° C. and a solution of 11.4 mL DEAD in 30 mL anhydrous THF was added dropwise over 20 min. The reaction was warmed to room temperature and stirred for 45 min. A solution of 11.3 mL 2-(2,4-Dichlorophenyl)-ethanol in 10 mL anhydrous THF was added with cooling. The reaction was stirred at room temperature for 16 h, then the solvents were removed under reduced pressure. The residue was treated with n-heptane:ethyl acetate/1:1. The filtrate was dried under reduced pressure. The product was purified by silica gel chromatography, eluting with n-heptane:ethyl acetate/4:1, then n-heptane:ethyl acetate/3:1. Yield 17 g.

(c) 3-[2-(2,4-Dichlorophenyl)-ethoxy]-4-methoxy-benzoic acid 17 g of 3-[2-(2,4-Dichlorophenyl)-ethoxy]-4-methoxy-benzoic acid methyl ester was dissolved in 200 mL of methanol:water/3:1. 4.1 g of lithium hydroxide monohydrate was added to the solution, and the reaction was stirred at room temperature for 16 h then at 90° C. for 2 h. The solution was cooled to room temperature, then acidified with half-concentrated hydrochloric acid. The solvents were removed under reduced pressure and the residue was washed twice with warm water to remove salts.

(d) A solution of 100 mg 3-[2-(2,4-Dichlorophenyl)-ethoxy]-4-methoxy-benzoic acid in 2 ml DMF was activated by the addition of 53 mg carbonyldiimidazole. After stirring for 2 h at RT 90 mg of 4-Aminomethyl-piperidine-1-carboxamidine hydrochloride and 2 ml DMSO were added and the mixture was stirred overnight. Subsequent dilution with 3 ml water and filtration through a chem elut® cartridge, eluting with ethyl acetate yielded after concentration under reduced pressure a white solid. Purification by preparative HPLC ($C_{18}$ reverse phase column, elution with a $H_2O$/MeCN gradient with 0.5% TFA) and lyophilisation afforded 30 mg (20%) of the title compound as a white powder.

MS (ESI +) m/e 479.3 (M+H) chloro pattern.

Example 12

3-[2-(2,4-Dichloro-phenyl)-ethoxy]-N-[1-(10-imino-ethyl)-piperidin-4-ylmethyl]-4-methyl-benzamide; compound with trifluoro-acetic acid

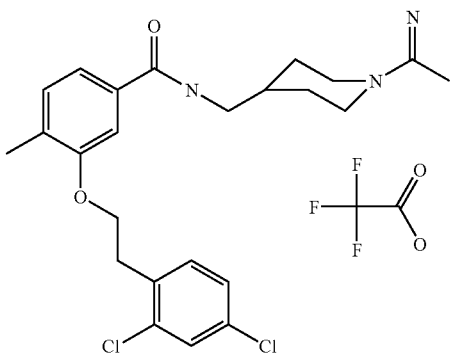

50 mg of 3-[2-(2,4-Dichloro-phenyl)-ethoxy]-4-methyl-benzoic acid and 58.9 mg of C-[1-(1-imino-ethyl)-piperidin-4-yl]-methylamine di-trifluoroacetic acid salt were dissolved in 5 ml of DMF. After cooling to 0° C. 64.3 mg of HATU and 70.8 mg of NEM were added. The mixture was stirred at 0° C. for 2 hours and at room temperature for 3 hours. The solvent was removed under reduced pressure and the residue was purified by preparative HPLC (C18 reverse phase column) (gradient acetonitrile water (containing 0.1% trifluoro-acetic acid) 90:10 to 0:100). The fractions containing the product were evaporated and lyophilized. Yield: 48 mg (54%), MS: 462.2/464.3 $(M+H)^+$.

Example 13

N-(1-Carbamimidoyl-piperidin-4-ylmethyl)-3-[2-(2,4-dichloro-phenyl)-ethoxy]-4-methyl-benzamide; compound with trifluoro-acetic acid

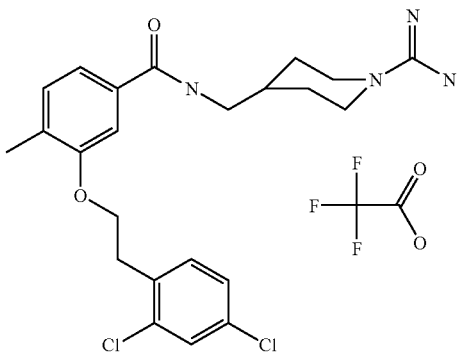

50 mg of 3-[2-(2,4-Dichloro-phenyl)-ethoxy]-4-methyl-benzoic acid and 35.2 mg of 4-aminomethyl-piperidine-1-carboxamidine dihydrochloride were dissolved in 5 ml of DMF. After cooling to 0° C. 64.3 mg of HATU and 70.8 mg of NEM were added. The mixture was stirred at 0° C. for 2 hours and at room temperature for 3 hours. The solvent was removed under reduced pressure and the residue was purified by preparative HPLC ($C_{18}$ reverse phase column) (gradient acetonitrile water (containing 0.1% trifluoro-acetic acid) 90:10 to 0:100). The fractions containing the product were evaporated and lyophilized.

Yield: 45 mg (51%), MS: 463.3/465.3 $(M+H)^+$.

Example 14

{Amino-[4-({3-[2-(2,4-dichloro-phenyl)-ethoxy]-4-methyl-benzoylamino}-methyl)-piperidin-1-yl]-methylene}-carbamic acid benzyl ester

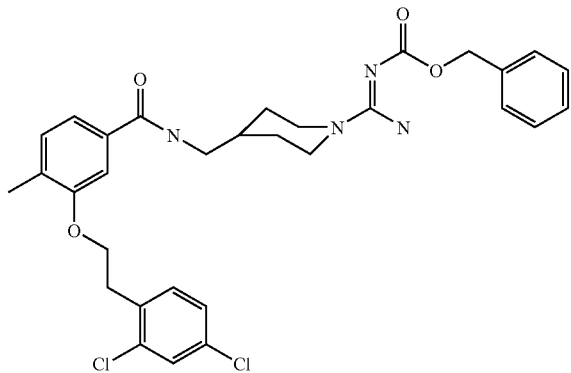

97 mg of 3-[2-(2,4-Dichloro-phenyl)-ethoxy]-4-methyl-benzoic acid and 124.3 mg of [Amino-(4-aminomethyl-piperidin-1-yl)-methylene]-carbamic acid benzyl ester trifluoro-acetic acid salt were dissolved in 5 ml of DMF. After cooling to 0° C. 136 mg of HATU and 106 mg of NEM were added. The mixture was stirred at 0° C. for 2 hours and at room temperature for 3 hours. The solvent was removed under reduced pressure and the residue was purified by preparative HPLC ($C_{18}$ reverse phase column) (gradient acetonitrile water (containing 0.1% trifluoro-acetic acid) 90:10 to 0:100). The fractions containing the product were evaporated and lyophilized.

Yield: 146 mg (79.5%), MS: 597.3/599.3 $(M+H)^+$.

Pharmacological Testing

The ability of the compounds of the formula I to inhibit factor Xa or factor VIIa or other enzymes like thrombin, plasmin, or trypsin can be assessed by determining the concentration of the compound of the formula I that inhibits enzyme activity by 50%, i. e. the $IC_{50}$ value, which is related to the inhibition constant Ki. Purified enzymes are used in chromogenic assays. The concentration of inhibitor that causes a 50% decrease in the rate of substrate hydrolysis is determined by linear regression after plotting the relative rates of hydrolysis (compared to the uninhibited control) versus the log of the concentration of the compound of formula I. For calculating the inhibition constant Ki, the $IC_{50}$ value is corrected for competition with substrate using the formula $Ki = IC_{50}/\{1+(\text{substrate concentration}/Km)\}$ wherein Km is the Michaelis-Menten constant (Chen and Prusoff, Biochem. Pharmacol. 22 (1973), 3099-3108; I. H. Segal, Enzyme Kinetics, 1975, John Wiley & Sons, New York, 100-125; which are incorporated herein by reference).

a) Factor Xa Assay

In the assay for determining the inhibition of factor Xa activity TBS-PEG buffer (50 mM Tris-HCl, pH 7.8, 200 mM NaCl, 0.05% (w/v) PEG-8000, 0.02% (w/v) $NaN_3$) was used. The $IC_{50}$ was determined by combining in appropriate wells of a Costar half-area microtiter plate 25 µl human factor Xa (Enzyme Research Laboratories, Inc.; South Bend, Ind.) in TBS-PEG; 40 µl 10% (v/v) DMSO in TBS-PEG (uninhibited control) or various concentrations of the compound to be tested diluted in 10% (v/v) DMSO in TBS-PEG; and substrate S-2765 (N($\alpha$)-benzyloxycarbonyl-D-Arg-Gly-L-Arg-p-nitroanilide; Kabi Pharmacia, Inc.; Franklin, Ohio) in TBS-PEG.

The assay was performed by pre-incubating the compound of formula I plus enzyme for 10 min. Then the assay was initiated by adding substrate to obtain a final volume of 100 µl. The initial velocity of chromogenic substrate hydrolysis was measured by the change in absorbance at 405 nm using a Bio-tek Instruments kinetic plate reader (Ceres UV900HDi) at 25° C. during the linear portion of the time course (usually 1.5 min after addition of substrate). The enzyme concentration was 0.5 nM and substrate concentration was 140 µM.

b) Factor VIIa Assay

The inhibitory activity towards factor VIIa/tissue factor activity was determined using a chromogenic assay essentially as described previously (J. A. Ostrem et al., Biochemistry 37 (1998) 1053-1059 which is incorporated herein by reference). Kinetic assays were conducted at 25° C. in half-area microtiter plates (Costar Corp., Cambridge, Mass.) using a kinetic plate reader (Molecular Devices Spectramax 250). A typical assay consisted of 25 µl human factor VIIa and TF (5 nM and 10 nM, respective final concentration) combined with 40 µl of inhibitor dilutions in 10% DMSO/TBS-PEG buffer (50 mM Tris, 15 mM NaCl, 5 mM $CaCl_2$, 0.05% PEG 8000, pH 8.15). Following a 15 minute preincubation period, the assay was initiated by the addition of 35 µl of the chromogenic substrate S-2288 (D-Ile-Pro-Arg-p-nitroanilide, Pharmacia Hepar Inc., 500 µM final concentration).

The following test results (inhibition constants Ki (FXa) for inhibition of factor Xa) were obtained:
Example 1: Ki(FXa) 2.116 micromolar
Example 2: Ki(FXa) 0.0137 micromolar
Example 3: Ki(FXa) 0.0585 micromolar
Example 4: Ki(FXa) 0.4635 micromolar
Example 6: Ki(FXa) 2.280 micromolar
Example 11: Ki(FXa) 0.189 micromolar
Example 12: Ki(FXa) 0.14 micromolar
Example 13: Ki(FXa) 0.173 micromolar
Example 14: Ki(FXa) 5.077 micromolar (Prodrug)

The invention claimed is:
1. A compound the following formula

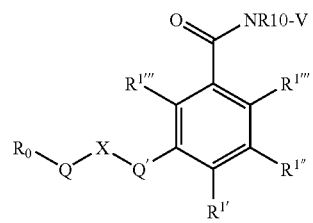

wherein
$R_0$ is phenyl, wherein the phenyl is disubstituted independently of one another by $R^2$;

$R^2$ is halogen, $(C_1-C_2)$-alkyloxy, wherein the alkyloxy is unsubstituted or substituted by amino, or —$(C_1-C_4)$-alkyl, wherein the alkyl is unsubstituted or substituted by amino;

one of Q and Q' is direct bond and the other is —O—;

$R_{10}$ is hydrogen;

X is —$CH_2$—$CH_2$—;

one of $R^{1\prime}$, $R^{1\prime\prime}$, $R^{1\prime\prime\prime}$, and $R^{1\prime\prime\prime\prime}$ is hydrogen, and the others are selected from hydrogen or $R^1$;

$R^1$ is halogen, —OH, —$NH_2$, —C(O)—$NR^{14}R^{15}$, or —$(C_1-C_3)$-alkyloxy, or —$(C_1-C_3)$-alkyl, wherein the alkyl of each group is unsubstituted or mono-, di- or trisubstituted independently of one another by $R^{13}$;

$R^{14}$ and $R^{15}$ are, independently, hydrogen or $(C_1-C_2)$-alkyl-;

$R^{13}$ is fluorine or chlorine;

V is a residue of formula

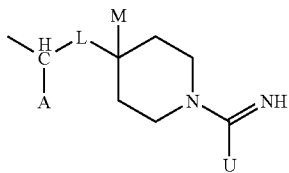

IIa

L is direct bond;

A is hydrogen, —C(O)—OH, —C(O)—O—$(C_1-C_4)$-alkyl, —C(O)—$NR^4R^5$ or —$(C_1-C_4)$-alkyl;

U is —$NH_2$, methyl, —NH—C(O)—O—$(C_1-C_4)$-alkyl or —NH—C(O)—O—$(CH_2)$-phenyl;

M is hydrogen; and $R^4$ and $R^5$ are independently of one another hydrogen or methyl;

or a stereoisomeric form or a mixture of stereoisomeric forms thereof in any ratio, or a physiologically tolerable salt thereof.

2. A process for preparing the compounds according to claim 1, comprising linking a building block of formula XI with a fragment of formula XII,

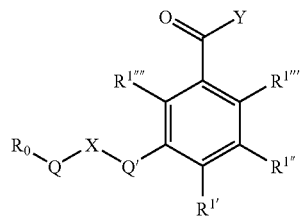

XI wherein $R_0$, Q, Q' and X, are as defined in claim 1,

R1', R1'', R1''' and R1'''' or $R_1$ are as defined in claim 1, and

Y is a nucleophilically substitutable leaving group or a hydroxyl group, wherein $R_0$, $R^1$, and X can also be present in protected form or in the form of precursor groups, and wherein the formula XII is $$H-NR^{10}-V \qquad (XII)$$

wherein R10 and V are as defined in claim 1, and can also be present in protected form or in the form of precursor groups.

3. A pharmaceutical composition comprising a therapeutically effective amount of at least one compound according to claim 1, or a stereoisomeric form or a mixture of stereoisomeric forms thereof in any ratio, or a physiologically tolerable salt thereof, and a pharmaceutically acceptable cartier.

4. A method of treating thrombosis in a host in need thereof comprising administering a therapeutically effective amount of the compound according to claim 1, or a stereoisomeric form or a mixture of stereoisomeric forms thereof in any ratio, or a physiologically tolerable salt thereof to the host.

5. The method of claim 4, wherein the thrombosis occurs as a result of at least one of thrombolytic therapy, surgery, a myocardial infarction, angina, or stroke.

* * * * *